United States Patent
Li et al.

(12) 
(10) Patent No.: US 6,521,658 B1
(45) Date of Patent: Feb. 18, 2003

(54) CELL PROLIFERATION INHIBITORS

(75) Inventors: Qun Li, Libertyville, IL (US); Hing Sham, Mundelein, IL (US); Keith W. Woods, Libertyville, IL (US); Beth A. Steiner, Remington, IN (US); Stephen L. Gwaltney, II, Lindenhurst, IL (US); Kenneth J. Barr, San Francisco, CA (US); Hovis M. Imade, Chicago, IL (US); Saul Rosenberg, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/579,705

(22) Filed: May 26, 2000

Related U.S. Application Data

(63) Continuation-in-part of application No. 60/136,542, filed on May 28, 1999.

(51) Int. Cl.[7] .................. A61K 31/405; C07D 209/04; A61P 43/00
(52) U.S. Cl. .................. 514/415; 548/469; 548/507
(58) Field of Search .............. 548/507, 469; 514/415

(56) References Cited

U.S. PATENT DOCUMENTS

| | | | |
|---|---|---|---|
| 4,876,267 A | * 10/1989 | Butina et al. | 514/415 |
| 5,444,036 A | 8/1995 | Iwasaki et al. | |
| 5,610,320 A | 3/1997 | Yoshino et al. | 549/72 |
| 5,721,246 A | 2/1998 | Yoshino et al. | 514/300 |
| 5,767,283 A | 6/1998 | Yoshino et al. | 548/469 |
| 5,840,991 A | 11/1998 | Yeng et al. | |
| 5,846,969 A | 12/1998 | Yoshino et al. | 514/211 |
| 5,854,274 A | 12/1998 | Yoshino et al. | 514/290 |

FOREIGN PATENT DOCUMENTS

| | | |
|---|---|---|
| EP | 0949238 | 10/1999 |
| GB | 1541318 | 2/1979 |
| GB | 1557622 | 12/1979 |
| JP | 8231505 | 8/1996 |
| WO | 9503279 | 2/1995 |
| WO | 9507276 | 3/1995 |
| WO | 9527699 | 10/1995 |
| WO | 9805315 | 2/1998 |
| WO | 9936391 | 7/1999 |

OTHER PUBLICATIONS

Baciocchi, et al., "Oxidations of Benzyl and Phenethyl Phenyl Sulfides. Implications for the Mechanism of the Microsomal and Biomimetic Oxidation of Sulfides." *Tetrahedron*, vol. 53, No. 36, 1997, pp. 12287–12298.

Cevasco, et al., "The Effect of Leaving Group Variation on Reactivity in the Dissociative Hydrolysis of Aryl 3,5–dimethyl–4–hydroxybenzenesulfonates." *J. Chem. Soc., Perkin Trans. 2*, 1997, pp. 2215–2218.

Hall, et al., "The Synthesis of Pyrido [4,3–b] carbazoles from Diphenylamine Derivatives: Alternative Routes to and Relay Syntheses of Ellipticines and Olivacines." *J. Chem. Soc., Perkin Trans. 1*, 1992, pp. 3439–3450.

Müller et al., "Dehydrierungs–Additions–Reaktionen MIT Aroxylen, I." *Liebigs Annalen Der Chemie*, vol. 673, 1964, pp. 40–59.

Suzuki, et al., "Direct Conversion of Benzyl Alcohols Into Benzyl Sulfides with Organic Disulfide/Disphosphorus Tetraiodide." *Chemistry Letters*, 1981, pp. 267–268.

Zakatov, et al., "Effect of Arenesulfonamide Group on the Nature of Substitution in the Aromatic Ring IV.* Reaction of Derivatives of 4–Sulfonamidophenol and 1,4–DI(Sulfonamido)Benzene with Nitrosating Agents." *Russian Journal of Organic Chemistry*, vol. 30, No. 2, 1994, pp. 303–306.

* cited by examiner

*Primary Examiner*—Joseph K. McKane
*Assistant Examiner*—Andrea D. Small
(74) *Attorney, Agent, or Firm*—B. Gregory Donner

(57) ABSTRACT

Compounds having formula (I)

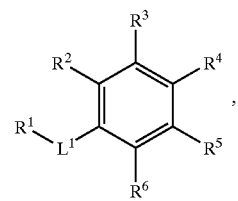

inhibit cellular proliferation. Processes for the preparation of the compounds, pharmaceutical compositions containing the compounds, and methods of treatment using the compounds are disclosed.

11 Claims, No Drawings

CELL PROLIFERATION INHIBITORS

CROSS REFERENCE TO RELATED APPLICATIONS

This application is a continuation-in-part of provisional U.S. Patent Application Ser. No. 60/136,542, filed May 28, 1999.

TECHNICAL FIELD

The present invention relates to compounds useful for treating pathological states which arise from or are exacerbated by cell proliferation, to pharmaceutical compositions comprising these compounds, and to methods of inhibiting cell proliferation in a mammal.

BACKGROUND OF THE INVENTION

Neoplastic diseases, characterized by the proliferation of cells which are not subject to normal cell proliferating controls, are a major cause of death in humans and other mammals. Cancer chemotherapy has provided new and more effective drugs to treat these diseases and has also demonstrated that drugs which disrupt microtubule synthesis are effective in inhibiting the proliferation of neoplastic cells.

Microtubules play a key role in the regulation of cell architecture, metabolism, and division. The microtubule system of eucaryotic cells comprises a dynamic assembly and disassembly matrix in which heterodimers of tubulin polymerize to form microtubules in both normal and neoplastic cells. Within noeplastic cells, tubulin is polymerized into microtubules which form the mitotic spindle. The microtubules are then depolymerized when the mitotic spindle's use has been fulfilled. Agents which disrupt the polymerization or depolymerization of microtubules in neoplastic cells, thereby inhibiting the proliferation of these cells, comprise some of the most effective cancer chemotherapeutic agents in use.

Because of the pivotal role played by cell proliferation, agents which inhibit microtubule polymerization have been the subject of active current research for their clinical potential. See, for example, U.S. Pat. Nos. 5,767,283, 5,721,246, 5,610,320, FR 2,729,421-A1, and WO96/27295. But there is still a need for tubulin polymerization-inhibiting compounds with modified or improved profiles of activity.

SUMMARY OF THE INVENTION

In one embodiment of the present invention are disclosed microtubule polymerization-inhibiting compounds represented by formula (I)

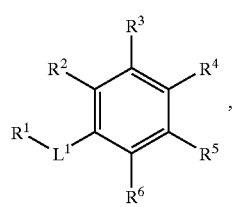

or pharmaceutically acceptable salts or prodrugs thereof, wherein
$L^1$ is selected from the group consisting of
(1) —S(O)$_2$O—,
(2) —OS(O)$_2$—,
(3) —NR$^7$SO$_2$—, wherein R$^7$ is selected from the group consisting of
  (a) hydrogen,
  (b) hydroxy,
  (c) amidinyl,
  (d) a nitrogen-protecting group,
  (e) alkanoyl,
  (f) alkyl,
  (g) alkenyl,
  (h) alkynyl,
  (i) cycloalkyl,
  (j) cycloalkylalkyl,
  (k) cycloalkenyl,
  (l) cycloalkenylalkyl,
  (m) aryloyl,
  (n) alkoxy,
  wherein (e)–(n) can be optionally substituted with one, two, or three substituents independently selected from the group consisting of
    (i) hydroxyl,
    (ii) halo,
    (iii) cyano,
    (iv) azido,
    (v) carboxy,
    (vi) amidinyl,
    (vii) alkyl,
    (viii) aryl,
    (ix) oxo,
    (x) heteroaryl,
    (xi) heterocycloalkyl,
    (xii) —NR$^c$R$^d$, wherein R$^c$ and R$^d$ are independently selected from the group consisting of
      (1') hydrogen,
      (2') alkyl,
      (3') aryl, and
      (4') alkoxyalkyl, and
    (xiii) -(alkylene)-NR$^c$R$^d$,
    wherein for (x) and (xi), the heteroaryl and the heterocycloalkyl can be optionally substituted with 1, 2, or 3 substituents independently selected from the group consisting of
      (1') alkyl, and
      (2') a nitrogen protecting group,
  (o) heterocycloalkyloyl, wherein the heterocycloalkyloyl can be optionally substituted with 1, 2, or 3 substituents independently selected from the group consisting of
    (i) alkyl, and
    (ii) a nitrogen protecting group, and
  (p) —(CH$_2$)$_x$NR$^A$R$^B$, wherein x is 0–6, and R$^A$ and R$^B$ are independently selected from the group consisting of
    (i) hydrogen,
    (ii) alkyl,
    (iii) alkenyl,
    (iv) alkynyl,
    (v) cycloalkyl,
    (vi) cycloalkylalkyl,
    (vii) cycloalkenyl, and
    (viii) cycloalkenylalkyl,
(4) —SO$_2$NR$^7$—, wherein R$^7$ is defined above,
(5) —S(O)CR$^{12}$R$^{13}$—, wherein R$^{12}$ and R$^{13}$ are independently selected from the group consisting of
  (a) hydrogen,
  (b) alkyl,
  (c) alkenyl, and
  (d) alkynyl, (6) —SO$_2$CR$^{12}$R$^{13}$—,
(7) —SCR$^{12}$R$^{13}$—,
(8) —CR$^{12}$R$^{13}$S(O)—,
(9) —CR$^{12}$R$^{13}$SO$_2$—, and
(10) —CR$^{12}$R$^{13}$S—,
wherein (1)–(10) are shown with their left ends attached to R$^1$ and their right ends attached to the phenyl ring;
R$^1$ is aryl or heteroaryl, wherein the aryl or the heteroaryl can be optionally substituted with 1, 2, 3, 4, or 5 substituents independently selected from the group consisting of
(a) oxo,
(b) azido,
(c) carboxy,
(d) carboxaldehyde,
(e) cyano,
(f) halo,
(g) hydroxy,
(h) nitro,
(i) perfluoroalkyl,
(j) perfluoroalkoxy,
(k) alkyl,
(l) alkenyl,
(m) alkynyl,
(n) alkanoyloxy,
(o) alkoxycarbonyl,
(p) cycloalkyl,
(q) cycloalkylalkyl,
(r) cycloalkenyl,
(s) cycloalkenylalkyl,
(t) alkanoyl,
(u) alkoxy,
(v) cycloalkoxy,
(w) aryloxy,
(x) heteroaryloxy,
(y) thioalkoxy
(z) alkylsulfinyl,
(aa) alkylsulfonyl,
(bb) —NR$^8$R$^9$, wherein R$^8$ and R$^9$ are independently selected from the group consisting of
 (i) hydrogen
 (ii) alkyl,
 (iii) arylalkyl, and
 (iv) alkanoyl, wherein the alkanoyl can be optionally substituted with 1 or 2 substituents independently selected from the group consisting of
  (1') halo
  (2') hydroxy, and
  (3') —NR$^{10}$R$^{11}$ wherein R$^{10}$ and R$^{11}$ are independently hydrogen or alkyl, and
(cc) —SO$_2$NR$^8$R$^9$, wherein R$^8$ and R$^9$ are defined above;
R$^2$ and R$^6$ are independently selected from the group consisting of
(1) hydrogen,
(2) alkyl,
(3) alkoxy,
(4) thioalkoxy; and
(5) hydroxy, and
R$^3$, R$^4$, and R$^5$ are independently selected from the group consisting of
(1) alkyl,
(2) alkoxy,
(3) thioalkoxy, and
(4) hydroxy;
all of the foregoing with the proviso that combinations wherein L$^1$ is —NR$^7$SO$_2$— and R$^1$ is
 (1) unsubstituted or substituted 1H-indoly-7-yl,
 (2) phenyl which is 2-monosubstituted with —NR$^8$R$^9$,
 (3) pyrid-3-yl which is 2-monosubstituted with —NR$^8$R$^9$, or
 (4) pyrimidin-5-yl which is 4-monosubstituted with —NR$^8$R$^9$, are excluded therefrom.

In a preferred embodiment of the invention are compounds wherein L$^1$ is —SO$_2$NR$^7$—, and R$^7$ is defined above.

In another preferred embodiment of the invention are compounds wherein R$^1$ is aryl.

In another preferred embodiment of the invention are compounds wherein R$^1$ optionally substituted heteroaryl, particularly N-methyl substituted 1H-indolyl.

In another preferred embodiment of the invention are compounds wherein R$^7$ is substituted alkanoyl, substituted aryloyl, or optionally substituted heterocycloalkyloyl.

In another preferred embodiment of the invention are compounds wherein L$^1$ is —NR$^7$SO$_2$—, and R$^7$ is defined above.

In another preferred embodiemtn of the invention are compounds wherein L$^1$ is —SO$_2$CR$^{12}$R$^{13}$—.

In another preferred embodiemtn of the invention are compounds wherein L$^1$ is —SCR$^{12}$R$^{13}$—.

In another preferred embodiemtn of the invention are compounds wherein L$^1$ is —CR$^{12}$R$^{13}$S(O)—.

In another preferred embodiemtn of the invention are compounds wherein L$^1$ is —CR$^{12}$R$^{13}$SO$_2$—.

In another preferred embodiemtn of the invention are compounds wherein L$^1$ is —CR$^{12}$R$^{13}$S—.

In yet another preferred embodiment of the invention are compounds wherein L$^1$ is —OSO$_2$—.

In still yet another preferred embodiment of the invention are compounds wherein L$^1$ is —SO$_2$O—.

In another embodiment of the invention are disclosed methods of inhibiting polymerization of tubulin in a mammal in recognized need of such treatment comprising administering an effective amount of a compound having formula (I).

In yet another embodiment of the invention are disclosed methods of treating cancer in a mammal in recognized need of such treatment comprising administering an effective amount of a compound having formula (I).

In still yet another embodiment of the invention are disclosed pharmaceutical compositions containing compounds having formula (I).

DETAILED DESCRIPTION OF THE INVENTION

Definition of Terms

The term "alkanoyl," as used herein, refers to an alkyl group attached to the parent molecular group through a carbonyl group. The alkanoyl groups of this invention can be optionally substituted.

The term "alkanoyloxy," as used herein, refers to an alkanoyl group attached to the parent molecular group through an oxygen atom.

The term "alkenyl," as used herein, refers to a monovalent straight or branched chain group of two to six carbon atoms containing at least one carbon-carbon double bond. The alkenyl groups of this invention can be optionally substituted.

The term "alkoxy," as used herein, refers to an alkyl group attached to the parent molecular group through an oxygen atom. The alkoxy groups of this invention can be optionally substituted.

The term "alkoxyalkyl," as used herein, refers to an alkoxy group attached to the parent molecular moiety through an alkyl group.

The term "alkoxycarbonyl," as used herein, refers to an alkoxy group attached to the parent molecular group through a carbonyl group.

The term "alkyl," as used herein, refers to a monovalent group of one to six carbon atoms derived from a straight or branched chain saturated hydrocarbon. The alkyl groups of this invention can be optionally substituted.

The term "alkylating agent," as used herein, represents a reagent capable of donating an alkyl group during the course of a reaction. Examples of alkylating agents include methyl triflate, dimethyl sulfate, iodomethane, bromobutane, bromopropane, and the like.

The term "alkylene," as used herein, refers to a saturated divalent hydrocarbon group derived from a straight or branched chain saturated hydrocarbon by the removal of two hydrogen atoms.

The term "alkylsulfinyl," as used herein, refers to an alkyl group attached to the parent molecular group through an —S(O)— group.

The term "alkylsulfonyl," as used herein, refers to an alkyl group attached to the parent molecular group through an —SO$_2$— group.

The term "alkynyl," as used herein, refers to a monovalent straight or branched chain group of two to six carbon atoms containing at least one carbon-carbon triple bond The alkynyl groups of this invention can be optionally substituted.

The term "amidinyl," as used herein, refers to an —NR$^{10}$R$^{11}$ group, wherein R$^{10}$ and R$^{11}$ are defined above, connected to the parent molecular group through an imine.

The term "aryl," as used herein, refers to a mono- or bicyclic-carbocyclic ring system having at least one aromatic ring. Aryl groups are exemplified by those derived from phenyl, naphthyl, 1,2-dihydronaphthyl, 1,2,3,4-tetrahydronaphthyl, fluorenyl, indanyl, indenyl, azulenyl, and troponyl. Bicyclic aryl groups of this invention can be attached to the parent molecular group through either a saturated or unsaturated part of the group. The aryl groups of this invention can be optionally substituted.

The term "arylalkyl," as used herein, refers to an alkyl group to which is attached at least one aryl group.

The term "aryloxy," as used herein, refers to an aryl group attached to the parent molecular group through an oxygen atom.

The term "aryloyl," as used herein, refers to an aryl group attached to the parent molecular moiety through a carbonyl group. The aryloyl groups of this invention can be optionally substituted.

The term "azido," as used herein, refers to —N$_3$.

The term "base," as used herein, represents a reagent capable of accepting protons during the course of a reaction. Examples of bases include carbonates such as potassium carbonate, potassium bicarbonate sodium carbonate, sodium bicarbonate, and cesium carbonate; halides such as cesium fluoride; phosphates such as potassium phosphate, potassium dihydrogen phosphate, and potassium hydrogen phosphate; hydroxides such as lithium hydroxide, sodium hydroxide, and potassium hydroxide; disilylamides such as lithium hexamethyldisilazide, potassium hexamethyldisilazide, and sodium hexamethyldisilazide; trialkylamines such as triethylamine and diisopropylamine; heterocyclic amines such as imidazole, pyridine, pyridazine, pyrimidine, and pyrazine; bicyclic amines such as DBN and DBU; and hydrides such as lithium hydride, sodium hydride, and potassium hydride. The base chosen for a particular conversion depends on the nature of the starting materials, the solvent or solvents in which the reaction is conducted, and the temperature at which the reaction is conducted.

The term "carboxaldehyde," as used herein, refers to —CHO.

The term "carbonyl," as used herein, refers to —C(O)—.

The term "carboxy," as used herein, refers to —CO$_2$H.

The term "cyano," as used herein, refers to —CN.

The term "cycloalkenyl," as used herein, refers to a monovalent cyclic or bicyclic hydrocarbon of four to twelve carbon atoms having at least one carbon-carbon double bond.

The term "cycloalkenylalkyl," as used herein, refers to an alkyl group, as defined herein, to which is attached at lease one cycloalkenyl group.

The term "cycloalkyl," as used herein, refers to a monovalent saturated cyclic hydrocarbon group of three to twelve carbon atoms.

The term "cycloalkylalkyl," as used herein, refers to an alkyl group, as defined herein, to which is attached at lease one cycloalkyl group.

The term "halo," as used herein, refers to —F, —Cl, —Br or —I.

The term "heteroaryl," as used herein, refers to a cyclic aromatic group having five or six ring atoms, wherein at least one ring atom is selected from the group consisting of oxygen, sulfur, and nitrogen, and the remaining ring atoms are carbon. The nitrogen atoms can be optionally quaternized, and the sulfur atoms can be optionally oxidized. Heteroaryl groups of this invention include those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, thiene, triazole, and tetrazole.

The term "heteroaryl," as used herein, also includes bicyclic or tricyclic rings, wherein any of the aforementioned heteroaryl rings is fused to one or two rings independently selected from the group consisting of an aryl ring, a cycloalkyl ring, a cycloalkenyl ring, and another monocyclic heteroaryl or heterocyaloalkyl ring. These bicyclic or tricyclic heteroaryls include those derived from benzo[b]furan, benzo[b]thiene, benzimidazole, cinnoline, imidazo[4,5-c]pyridine, quinazoline, thieno[2,3-c]pyridine, thieno[3,2-b]pyridine, thieno[2,3-b]pyridine, indolizine, imidazo[1,2-a]pyridine, quinoline, isoquinoline, phthalazine, quinoxaline, naphthyridine, quinolizine, indole, isoindole, indazole, indoline, benzoxazole, benzopyrazole, benzothiozole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazine, phenoxazine, 1,2-dihydropyrrolo[3,2,1-hi]indole, indolizine, imidazo[1,2-a]pyridine, imidazo[1,5-a]pyridine, imidazo[1,2-a]pyridine, pyrido[1,2-a]indole, 10,11-dihydro-5H-dibenzo[b,e][1,4]diazepine, 5,11-dihydrodibenzo[b,e][1,4]oxazepine, and 2(1H)-pyridinone. The bicyclic or tricyclic heteroaryl rings and can be attached to the parent molecular group through either the heretoaryl group itself or the aryl, cycloalkyl, cycloalkenyl, or heterocycloalkyl group to which it is fused.

The term "heteroaryl," as used herein, also includes compounds having formula

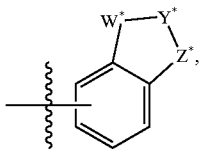

wherein W* is —O— or —NR$^{10}$—, wherein R$^{10}$ is defined above, Y* is —C(O)— or —(C(R$^{10}$)(R$^{11}$))$_v$—, wherein R$^{10}$ and R$^{11}$ are defined above, and v is 1, 2, or 3, and Z* is —CH$_2$—, —O—, —CH$_2$S(O)$_t$—, wherein t is zero, one or two, —CH$_2$O—, —CH$_2$NR$^{10}$—, or —NR$^{10}$—, wherein R$^{10}$ is defined above. The heteroaryl groups of this invention can be optionally substituted.

The term "heteroaryloxy," as used herein, refers to a heteroaryl group attached to the parent molecular group through an oxygen atom. The heteroaryloxy groups of this invention can be optionally substituted.

The term "heterocycloalkyl," as used herein, refers to a non-aromatic five-, six- or seven-membered ring having between one and three heteroatoms independently selected from oxygen, sulfur, and nitrogen, wherein each 5-membered ring has zero to one double bonds and each six-membered ring has zero to 2 double bonds. Representative heterocycloalkyl groups include 3,4-dihydropyridinyl, pyrrolidinyl, piperidinyl, piperazinyl, morpholinyl, tetrahydrofuryl, and 1,2,3,4-tetrahydropyridinyl. The heterocycloalkyl groups of this invention can be optionally substituted.

The term "heterocycloalkyloyl," as used herein, refers to a heterocycloalkyl group attached to the parent molecular moiety through a carbonyl group.

The term "hydroxy," as used herein, refers to —OH.

The term "imine," as used herein, refers to —C(=NR$^{21}$)—, wherein R$^{21}$ is defined above.

The term "nitro," as used herein, refers to —NO$_2$.

The term "nitrogen-protecting group," as used herein, refers to groups intended to protect an amino group against undesirable reactions during synthetic procedures. Commonly used nitrogen-protecting groups are disclosed in Greene, "Protective Groups In Organic Synthesis," (John Wiley & Sons, New York (1991)). Common N-protecting groups comprise (a) acyl groups such as formyl, acetyl, propionyl, pivaloyl, tert-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl and 4-nitrobenzoyl, (b) sulfonyl groups such as benzenesulfonyl, and para-toluenesulfonyl, (c) carbamate forming groups such as benzyloxycarbonyl, para-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, tert-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, cyclopentyloxycarbonyl, adamantyloxycarbonyl, cyclohexyloxycarbonyl, and phenylthiocarbonyl, (d) aralkyl groups such as benzyl, triphenylmethyl, and benzyloxymethyl, and (e) silyl groups such as trimethylsily. Preferred N-protecting groups are formyl, acetyl, benzoyl, pivaloyl, tert-butylacetyl, phenylsulfonyl, benzyl, tert-butyloxycarbonyl (Boc) and benzyloxycarbonyl (Cbz).

The term "oxo," as used herein, refers to (=O).

The term "perfluoroalkyl," as used herein, refers to an alkyl group in which all of the hydrogen atoms have been replaced by fluorine atoms.

The term "perfluoroalkoxy," as used herein, refers to a perfluoroalkyl group attached to the parent molecular group through an oxygen atom.

The term "perfluoroalkyl," as used herein, refers to an alkyl group in which all of the hydrogen atoms have been replaced by fluoride atoms.

The term "pharmaceutically acceptable salt," as used herein, refers to salts which are, within the scope of sound medical judgment, suitable for use in contact with the tissues of humans and lower animals without undue toxicity, irritation, or allergic response and are commensurate with a reasonable benefit/risk ratio. Pharmaceutically acceptable salts are well-known in the art. For example, S. M. Berge, et al. describe pharmaceutically acceptable salts in detail in J. Pharmaceutical Sciences, 1977, 66: 1 et seq, hereby incorporated by reference. The salts may be prepared in situ during the final isolation and purification of the compounds of the invention or separately by reacting a free base function with a suitable acid. Representative acid addition salts include acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl, and stearyl chlorides, bromides and iodides; and arylalkyl halides such as benzyl and phenethyl bromides. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term "pharmaceutically acceptable prodrugs," as used herein refers to, those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to parent compounds having formula (I), for example, by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are hereby incorporated by reference. Particularly preferred prodrugs of the invention include compounds having formula (I), wherein a nitrogen, hydroxy, or thiol group has attached thereto an aminoacyl, bisaminoacyl (2-mer), or trisaminoacyl (3-mer) group optionally capped with a carboxyl protecting group. The term "aminoacyl," as used herein, refers to a group derived from naturally or unnaturally occuring amino acids. Representative aminoacyl groups include those derived from glycine, alanine, β-alanine, valine, leucine, iso-leucine, methionine, serine, threonine, cysteine, phenylalanine, and tyrosine in the racemic, D or L configurations. The aminoacyl groups of this invention can be optionally substituted. The terms "bisaminoacyl" and "trisaminoacyl," as used herein, refer to di- and tri-aminoacyl groups, respectively. Representative examples of bisaminoacyl and trisaminoacyl groups include 2-mers and 3-mers derived from glycine, alanine, β-alanine, valine, leucine, iso-leucine, methionine, serine, threonine, cysteine, phenylalanine, and tyrosine in the racemic, D or L configurations.

The term "thioalkoxy," as used herein, refers to an alkyl group attached to the parent molecular group through a sulfur atom.

The present invention contemplates metabolites formed by in vivo biotransformation of compounds having formula (I). The term "metabolite," as used herein, refers to compounds formed by in vivo biotransformation of compounds having formula (I) by oxidation, reduction, hydrolysis, or conjugation. The present invention also contemplates compounds which undergo in vivo biotransformation such as by oxidation, reduction, hydrolysis, or conjugation to form compounds having formula (I). A thorough discussion of biotransformation is provided in Goodman and Gilman's, *The Pharmacological Basis of Therapeutics,* seventh edition, hereby incorporated by reference.

Asymmetric or chiral centers may exist in the compounds of the present invention. The present invention contemplates the various stereoisomers and mixtures thereof. Individual stereoisomers of compounds of the present invention are prepared synthetically from commercially available starting materials which contain asymmetric or chiral centers or by preparation of mixtures of enantiomeric compounds followed by resolution well-known to those of ordinary skill in the art. These methods of resolution are exemplified by (1) attachment of a racemic mixture of enantiomers to a chiral auxiliary, separation of the resulting diastereomers by recrystallization or chromatography and liberation of the optically pure product from the auxiliary or (2) direct separation of the mixture of optical enantiomers on chiral chromatographic columns.

Geometric isomers may also exist in the compounds of the present invention. The present invention contemplates the various geometric isomers and mixtures thereof resulting from the arrangement of substituents around a carbon-carbon double bond.

Compounds falling within the scope of formula (I) include, but are not limited to 4-methoxy-N-(3,4,5-trimethoxyphenyl) benzenesulfonamide,
3,4-dimethoxy-N-(3,4,5-trimethoxyphenyl) benzenesulfonamide,
4-trifluoromethoxy-N-(3,4,5-trimethoxyphenyl) benzenesulfonamide,
4-trifluoromethyl-N-(3,4,5-trimethoxyphenyl) benzenesulfonamide,
4-nitro-N-(3,4,5-trimethoxyphenyl)benzenesulfonamide,
4-amino-N-(3,4,5-trimethoxyphenyl)benzenesulfonamide,
4-((2-chloroacetyl)amino)-N-(3,4,5-trimethoxyphenyl) benzenesulfonamide,
2-nitro-N-(3,4,5-trimethoxyphenyl)benzenesulfonamide,
4-methoxy-3-nitro-N-(3,4,5-trimethoxyphenyl) benzenesulfonamide,
3-amino-4-methoxy-N-(3,4,5-trimethoxyphenyl) benzenesulfonamide,
1-formyl-N-(3,4,5-trimethoxyphenyl)indoline-5-sulfonamide,
N-(3,4,5-trimethoxyphenyl)indoline-5-sulfonamide,
5-nitro-N-(3,4,5-trimethoxyphenyl)-1H-indole-3-sulfonamide,
1-methyl-N-(3,4,5-trimethoxyphenyl)indoline-5-sulfonamide,
1-methyl-5-nitro-N-(3,4,5-trimethoxyphenyl)-1H-indole-3-sulfonamide,
5-amino-1-methyl-N-(3,4,5-trimethoxyphenyl)-1H-indole-3-sulfonamide,
5-amino-N-(3,4,5-trimethoxyphenyl)-1H-indole-3-sulfonamide,
N-(3,4,5-trimethoxyphenyl)-1H-indole-5-sulfonamide,
1-methyl-N-(3,4,5-trimethoxyphenyl)-1H-indole-5-sulfonamide,
N,1-dimethyl-N-(3,4,5-trimethoxyphenyl)-1H-indole-5-sulfonamide,
3,4,5-trimethoxy-N-(4-methoxyphenyl) benzenesulfonamide,
N-(3-hydroxy-4-methoxyphenyl)-3,4,5-trimethoxybenzenesulfonamide,
N-(1-methyl-1H-indol-5-yl)-3,4,5-trimethoxybenzenesulfonamide,
N-(4-(dimethylamino)phenyl)-3,4,5-trimethoxybenzenesulfonamide,
N-(4-fluoro-3-methoxyphenyl)-3,4,5-trimethoxybenzenesulfonamide,
3,4,5-trimethoxy-N-(4-(trifluoromethoxy)phenyl) benzenesulfonamide,
3,4,5-trimethoxy-N-(2,3,4,5,6-pentafluorophenyl) benzenesulfonamide,
N-(3-amino-4-methoxyphenyl)-3,4,5-trimethoxybenzenesulfonamide,
3,4,5-trimethoxy-N-(1-methyl-1H-indol-4-yl) benzenesulfonamide,
3,4,5-trimethoxy-N-(1-methyl-1H-indol-6-yl) benzenesulfonamide, N-(1H-indol-5-yl)-3,4,5-trimethoxybenzenesulfonamide,
N-(1,2-dimethyl-1H-indol-5-yl)-3,4,5-trimethoxybenzenesulfonamide,
N-(3-chloro-1H-indol-5-yl)-3,4,5-trimethoxybenzenesulfonamide,
N-(1H-indazol-5-yl)-3,4,5-trimethoxybenzenesulfonamide,
3,4,5-trimethoxy-N-(1-methyl-1H-benzimidazol-6-yl)benzenesulfonamide,
3,4,5-trimethoxy-N-(1-methyl-1H-benzimidazol-5-yl)benzenesulfonamide,
3,4,5-trimethoxy-N-methyl-N-(1-methyl-1H-indol-5-yl)benzenesulfonamide, 3,4,5-trimethoxy-N-(2-(dimethylamino)ethyl)-N-(1-methyl-1H-indol-5-yl)benzenesulfonamide,
1H-indol-5-yl 3,4,5-trimethoxybenzenesulfonate,
(3,4,5-trimethoxyphenyl) 4-methoxybenzenesulfonate,
3,4,5-trimethoxyphenyl) 4-methylbenzenesulfonate,
1H-indol-5-yl 3,4,5-trimethoxybenzenesulfonate,
3,4,5-trimethoxyphenyl) 3-amino-4-methoxybenzenesulfonate,
(3,4,5-trimethoxyphenyl)-4-(dimethylamino)benzenesulfonate,
4-methylphenyl 3,4,5-trimethoxybenzenesulfonate,
3,4,5-trimethoxyphenyl 1-methyl-5-indolinesulfonate, and
4-methoxyphenyl 3,4,5-trimethoxybenzenesulfonate.
tert-butyl 2-((1-methyl-1H-indol-5-yl)((3,4,5-trimethoxyphenyl)sulfonyl)amino)ethylcarbamate,
N-(2-hydroxyethyl)-3,4,5-trimethoxy-N-(1-methyl-1H-indol-5-yl)benzenesulfonamide,
N-(2,3-dihydro-1,4-benzodioxin-6-yl)-3,4,5-trimethoxybenzenesulfonamide,
N-(2-aminoethyl)-3,4,5-trimethoxy-N-(1-methyl-1H-indol-5-yl)benzenesulfonamide,
3-amino-4-methoxy-N-methyl-N-(3,4,5-trimethoxyphenyl)benzenesulfonamide,
1-ethyl-N-(3,4,5-trimethoxyphenyl)-1H-indole-5-sulfonamide,
N-acetyl-3,4,5-trimethoxy-N-(1-methyl-1H-indol-5-yl)benzenesulfonamide,
3,4,5-trimethoxy-N-(6-quinolinyl)benzenesulfonamide,
N-(2-hydroxyethyl)-1-methyl-N-(3,4,5-trimethoxyphenyl)-1H-indole-5-sulfonamide,
N-(2-fluoroethyl)-1-methyl-N-(3,4,5-trimethoxyphenyl)-1H-indole-5-sulfonamide,
N-ethyl-1-methyl-N-(3,4,5-trimethoxyphenyl)-1H-indole-5-sulfonamide,
4-nitrophenyl-3,4,5-trimethoxybenzenesulfonate,
4-aminophenyl-3,4,5-trimethoxybenzenesulfonate,
4-dimethylaminophenyl-3,4,5-trimethoxybenzenesulfonate,
3,4,5-trimethoxyphenyl 6-methoxy-3-pyridinesulfonate,
1-methyl-2-oxo-1,2-dihydro-4-pyridinyl 3,4,5-trimethoxybenzenesulfonate.
3,4,5-trimethoxyphenyl 3-((3-aminopropanoyl)amino)-4-methoxybenzenesulfonate,
3,4,5-trimethoxyphenyl 3-(((2R)-2-aminopropanoyl)amino)-4-methoxybenzenesulfonate,
3,4,5-trimethoxyphenyl 3-(((2R)-2-amino-3-methylbutanoyl)amino)-4-methoxybenzenesulfonate,
N-((dimethylamino)acetyl)-1-methyl-N-(3,4,5-trimethoxyphenyl)-1H-indole-5-sulfonamide,
1-methyl-N-(((2S)-1-methylpyrrolidinyl)carbonyl)-N-(3,4,5-trimethoxyphenyl)-1H-indole-5-sulfonamide,
N-((2S)-2-(dimethylamino)-3-methylbutanoyl)-1-methyl-N-(3,4,5-trimethoxyphenyl)-1H-indole-5-sulfonamide,
N-((2S)-2-amino-3-methylbutanoyl)-1-methyl-N-(3,4,5-trimethoxyphenyl)-1H-indole-5-sulfonamide,
1-methyl-N-(((2S)-2-methylamino)propanoyl)-N-(3,4,5-trimethoxyphenyl)-1H-indole-5-sulfonamide,
N-((2S)-2-amino-2-phenylethanoyl)-1-methyl-N-(3,4,5-trimethoxyphenyl)-1H-indole-5-sulfonamide,
N-((2S)-2-amino-3-phenylpropanoyl)-1-methyl-N-(3,4,5-trimethoxyphenyl)-1H-indole-5-sulfonamide,
1-methyl-N-(((2S)-pyrrolidinylcarbonyl)-N-(3,4,5-trimethoxyphenyl)-1H-indole-5-sulfonamide,
N-((2S)-2,6-diaminohexanoyl)-1-methyl-N-(3,4,5-trimethoxyphenyl)-1H-indole-5-sulfonamide,
N-((2S)-2-amino-3-(1H-imidazol-5-yl)propanoyl)-1-methyl-N-(3,4,5-trimethoxyphenyl)-1H-indole-5-sulfonamide,
(2S)-2-amino-4-oxo-4-(3,4,5-trimethoxy((1-methyl-1H-indol-5-yl)sulfonyl)anilino)butanoic acid,
(3S)-3-amino-4-oxo-4-(3,4,5-trimethoxy((1-methyl-1H-indol-5-yl)sulfonyl)anilino)butanoic acid,
(2S)-2-amino-5-oxo-5-(3,4,5-trimethoxy((1-methyl-1H-indol-5-yl)sulfonyl)anilino)pentanoic acid,
(4S)-4-amino-5-oxo-5-(3,4,5-trimethoxy((1-methyl-1H-indol-5-yl)sulfonyl)anilino)pentanoic acid,
N-((bis(2-methoxyethyl)amino)acetyl)-1-methyl-N-(3,4,5-trimethoxyphenyl)-1H-indole-5-sulfonamide,
1-methyl-N-(4-morpholinylacetyl)-N-(3,4,5-trimethoxyphenyl)-1H-indole-5-sulfonamide,
1-methyl-N-((4-methyl-1-piperazinyl)acetyl)-N-(3,4,5-trimethoxyphenyl)-1H-indole-5-sulfonamide,
N-(4-(aminomethyl)benzoyl)-1-methyl-N-(3,4,5-trimethoxyphenyl)-1H-indole-5-sulfonamide,
1,2,3-trimethoxy-5-((4-methoxybenzyl)sulfanyl)benzene,
1,2,3-trimethoxy-5-((4-methoxybenzyl)sulfinyl)benzene,
1,2,3-trimethoxy-5-((4-methoxybenzyl)sulfonyl)benzene,
1,2,3-trimethoxy-5-((1-(4-methoxyphenyl)-1-methylethyl)sulfonyl)benzene,
2-methoxy-5-(((3,4,5-trimethoxyphenyl)sulfanyl)methyl)aniline,
2-methoxy-5-(((3,4,5-trimethoxyphenyl)sulfinyl)methyl)aniline,
2-methoxy-5-(((3,4,5-trimethoxyphenyl)sulfonyl)methyl)aniline,
2-methoxy-5-(1-methyl-1-((3,4,5-trimethoxyphenyl)sulfonyl)ethyl)aniline,
1,2,3-trimethoxy-5-(((4-methoxyphenyl)sulfanyl)methyl)benzene,
1,2,3-trimethoxy-5-(((4-methoxyphenyl)sulfonyl)methyl)benzene,
1,2,3-trimethoxy-5-(1-((4-methoxyphenyl)sulfonyl)-1-methylethyl)benzene,
2-methoxy-5-((3,4,5-trimethoxybenzyl)sulfonyl)aniline,
2-methoxy-5-((1-methyl-1-(3,4,5-trimethoxyphenyl)ethyl)sulfonyl)aniline, 1,2,3-trimethoxy-5-((phenylsulfonyl)methyl)benzene,
N-(2-aminoacetyl)-1-methyl-N-(3,4,5-trimethoxyphenyl)-1H-indole-5-sulfonamide,
N-(2-aminoacetyl)-3,4,5-trimethoxy-N-(1-methyl-1H-indol-5-yl)benzenesulfonamide,
N-((2S)-2-aminopropanoyl]-1-methyl-N-(3,4,5-trimethoxyphenyl)-1H-indole-5-sulfonamide,
N-((2S)-2-aminopropanoyl]-3,4,5-trimethoxy-N-(1-methyl-1H-indol-5-yl)benzenesulfonamide,
N-(3-aminopropanoyl)-1-methyl-N-(3,4,5-trimethoxyphenyl)-1H-indole-5-sulfonamide,
N-(3-aminopropanoyl)-3,4,5-trimethoxy-N-(1-methyl-1H-indol-5-yl)benzenesulfonamide,
(2S)-2-amino-N-((1S)-1-methyl-2-oxo-2-(3,4,5-trimethoxy((1-methyl-1H-indol-5-yl)sulfonyl)anilino)ethyl)propanamide,
(2S)-2-amino-N-((1S)-1-methyl-2-((1-methyl-1H-indol-5-yl)((3,4,5-trimethoxyphenyl)sulfonyl)amino)-2-oxoethyl)propanamide, N-((2S)-2-amino-3-hydroxypropanoyl)-1-methyl-N-(3,4,5-trimethoxyphenyl)-1H-indole-5-sulfonamide, and
N-((2S)-2-amino-3-hydroxypropanoyl)-3,4,5-trimethoxy-N-(1-methyl-1H-indol-5-yl)benzenesulfonamide.

A more preferred compound for the practice of the present invention is N-((dimethylamino)acetyl)-1-methyl-N-(3,4,5-trimethoxyphenyl)-1H-indole-5-sulfonamide.

Determination of Biological Activity

Compounds of this invention were tested in a 48-hour cellular proliferation assay which uses human colon adenocarcinoma, MDR positive (HCT-15) cells, and human lung large cell carcinoma, MDR negative (NCI-H460) cells, in the 96-well microtitre format described in Skehan P., et al. New Colorimetric Cytotoxicity Assay for Anticancer Drug Screening. 1990, J. Natl. Cancer Inst. 82:1107–1112, hereby incorporated by reference. Briefly, the wells of a microtitre plate were charged sequentially with cultured cells and compounds of the invention ($1.0 \times 10^{-4}$ to $1.0 \times 10^{-11}$ M in 10% DMSO prepared by dissolving compounds of the invention in DMSO and adding 11 µL of the DMSO solution to 100 µL of culture medium for a final DMSO concentration of 10%). Two of the following controls were also present in each microtitre plate: a solvent (DMSO) control without drug that yielded a 0% inhibition level and a trichloroacetic acid-treated well that yielded a 100% inhibition level. The cells were grown in culture (37° C., 5% $CO_2$ atmosphere) for 48 hours then fixed by the addition of trichloroacetic acid. The wells were stained with sulforhodamine, washed with 1% acetic acid, and treated with 0.01M tris buffer (100 µL) to solubilize the adherent dye. The absorbance of the dye solution was measured with a Molecular Devices Spectra-Max340 plate reader. The percent inhibition values were obtained by calculating the proportional response of the experimental values to the absorbance values of the controls. The results for representative examples of compounds having formula (I) are shown in Table 1.

TABLE 1

Inhibitory Potency of Representative Compounds

| Example | NCI-460 % inhibition at $10^{-4}$ M | HCT-15 % inhibition at $10^{-4}$ M |
|---|---|---|
| 1 | 98.5 | 99.4 |
| 2 | 99.6 | >95 |
| 3 | 100.0 | 94.4 |
| 4 | 99.8 | 82.6 |
| 5 | 99.9 | 68.5 |
| 6 | >95 | 54.8 |
| 7 | 89.2 | 96.7 |
| 8 | 50.0 | 53.8 |
| 9 | 47.4 | 77.2 |
| 10 | 99.6 | 99.8 |
| 11 | 74.0 | 79.9 |
| 12 | 59.3 | 86.2 |
| 13 | 41.7 | 15.9 |
| 14 | 96.1 | 97.6 |
| 15 | 45.5 | 50.6 |
| 16 | 87.0 | 91.9 |
| 17 | <9.1 | 37.0 |
| 18 | 89.1 | 94.1 |
| 19 | 100.0 | 100.0 |
| 20 | 99.9 | 100.0 |
| 21 | 96.0 | 97.8 |
| 22 | 99.5 | 99.8 |
| 23 | 100.0 | 100.0 |
| 24 | 92.0 | 95.8 |
| 25 | 57.8 | 62.1 |
| 26 | 46.7 | 70.9 |
| 27 | 61.6 | 57.0 |
| 28 | 99.8 | 99.9 |
| 29 | 90.8 | 95.1 |
| 30 | 83.8 | 94.9 |
| 31 | 95.1 | 98.6 |
| 32 | 99.8 | 99.8 |
| 33 | 2.8 | 92.0 |
| 34 | 18.5 | 47.6 |
| 35 | 34.5 | 65.2 |
| 36 | 99.5 | 99.3 |
| 37 | 100.0 | 99.9 |
| 38 | 81.0 | 87.5 |
| 39 | 100.0 | 100.0 |
| 40 | 99.9 | 99.9 |
| 41 | 99.5 | 99.8 |
| 42 | 100.0 | 100.0 |
| 43 | 100.0 | 100.0 |
| 44 | 99.9 | 100.0 |
| 45 | 99.4 | 99.9 |
| 46 | 99.5 | 99.6 |
| 47 | 99.9 | 100.0 |
| 85 | 99.6 | 99.8 |
| 86 | 96.5 | 99.4 |
| 87 | 99.6 | 99.9 |
| 88 | 58.4 | 85.5 |
| 89 | 99.9 | 99.9 |
| 90 | 99.8 | 99.5 |
| 91 | 99.8 | 95.0 |
| 92 | 9.1 | 67.1 |
| 93 | 98.6 | 99.9 |
| 94 | 90.1 | 97.7 |
| 95 | 9.1 | 84.8 |
| 96 | 99.9 | 99.8 |

As shown by the data in Table 1, the compounds of the invention, including, but not limited to, those specified in the examples, are useful for the treatment of disease caused or exascerbated by cell proliferation. As cell proliferation inhibitors, these compounds are useful in the treatment of both primary and metastatic solid tumors and carinomas of the breast, colon, rectum, lung, oropharynx, hypopharynx, esophagus, stomach, pancreas, liver, gallbladder, bile ducts, small intestine, urinary tract including kidney, bladder and urothelium, female genital tract including cervix, uterus, ovaries, choriocarcinoma, and gestational trophoblastic disease, male genital tract including prostate, seminal vesicles, testes, and germ cell tumors, endocrine glands including thyroid, adrenal, and pituitary, skin including hemangiomas, melanomas, sarcomas arising from bone or soft tissues including Kaposi's sarcoma, tumors of the brain, nerves, and eyes, meninges including astrocytomas, gliomas, glioblastomas, retinoblastomas, neuromas, neuroblastomas, Schwannomas and meningiomas, solid tumors arising from hematopoietic malignancies including leukemias and chloromas, plasmacytomas, plaques, tumors of mycosis fungoides, cutaneous T-cell lymphoma/leukemia, lymphomas including Hodgkin's and non-Hodgkin's lymphomas, prophylaxis of autoimmune diseases including rheumatoid, immune and degenerative arthritis, ocular diseases including diabetic retinopathy, retinopathy of prematurity, corneal graft rejection, retrolental fibroplasia, neovascular glaucoma, rubeosis, retinal neovascularization due to macular degeneration, hypoxia, abnormal neovascularization conditions of the eye, skin diseases including psoriasis, blood vessel diseases including hemagiomas and capillary proliferation within atherosclerotic plaques, Osler-Webber Syndrome, myocardial angiogenesis, plaque neovascularization, telangiectasia, hemophiliac joints, angiofibroma, and wound granulation.

The compounds of the present invention may also be useful for the prevention of metastases from the tumors described above either when used alone or in combination with radiotherapy and/or other chemotherapeutic treatments conventionally administered to patients for treating cancer. For example, when used in the treatment of solid tumors, compounds of the present invention may be administered with chemotherapeutic agents such as alpha inteferon, COMP (cyclophosphamide, vincristine, methotrexate, and prednisone), etoposide, mBACOD (methortrexate, bleomycin, doxorubicin, cyclophosphamide, vincristine, and dexamethasone), PRO-MACE/MOPP (prednisone, methotrexate (w/leucovin rescue), doxorubicin, cyclophosphamide, paclitaxel, etoposide/mechlorethamine, vincristine, prednisone, and procarbazine), vincristine, vinblastine, angioinhibins, TNP-470, pentosan polysulfate, platelet factor 4, angiostatin, LM-609, SU-101, CM-101, Techgalan, thalidomide, SP-PG, and the like. Other chemotherapeutic agents include alkylating agents such as nitrogen mustards (mechloethamine, melphan, chlorambucil, cyclophosphamide and ifosfamide), nitrosoureas including carmustine, lomustine, semustine and streptozocin, alkyl sulfonates including busulfan, triazines including dacarbazine, ethyenimines including thiotepa and hexamethylmelamine, folic acid analogs including methotrexate, pyrimidine analogues including 5-fluorouracil and cytosine arabinoside, purine analogs including 6-mercaptopurine and 6-thioguanine, antitumor antibiotics including actinomycin D, anthracyclines including doxorubicin, bleomycin, mitomycin C and methramycin, hormones and hormone antagonists including tamoxifen, cortiosteroids and miscellaneous agents including cisplatin and brequinar. For example, a tumor may be treated conventionally with surgery, radiation, or chemotherapy, and compounds having formula (I), then treated with additional compound having formula (I) to extend the dormancy of micrometastases and to stabilize and inhibit the growth of any residual primary tumor.

Methods of Treatment

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention. Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Synthetic Methods

The compounds and processes of the present invention will be better understood in connection with the following synthetic schemes, which illustrate methods by which the compounds of the invention may be prepared. The compounds having formula (I) may be prepared by a variety of synthetic routes. Representative procedures are shown in Scheme 1. The groups $R^1$, $R^2$, $R^3$, $R^4$, $R^5$, $R^6$, $R^{12}$, $R^{13}$, and $L^1$, are as previously defined unless otherwise noted. It will be readily apparent to one of ordinary skill in the art that other compounds within formula (I) can be synthesized by substitution of the appropriate reactants and agents in the syntheses shown below. It will further be apparent to one skilled in the art that the selective protection and deprotection steps, as well as order of the steps themselves, can be carried out in varying order, depending on the nature of groups $R^1$, $R^2$, $R^3$, $R^4$, $R^5$, $R^6$, $R^{12}$, $R^{13}$, and $L^1$, to successfully complete the syntheses of compounds having formula (I). Commonly used protecting groups are disclosed in Greene, "Protective Groups In Organic Synthesis," John Wiley & Sons, New York (1981), hereby incorporated by reference. It will still further be apparent to one of ordinary skill in the art that the substituents $R^1$, $R^2$, $R^3$, $R^4$, $R^5$, $R^6$, $R^{12}$, $R^{13}$, and $L^1$ can be determined by selection of the appropriate commercially available or known starting materials or introduced synthetically by known chemical methods such as those disclosed in Larock, "Comprehensive Organic Transformations. A Guide to Functional Group Preparations," VCH Publishers, New York (1989), hereby incorporated by reference.

Abbreviations

Abbreviations used in the descriptions of the schemes the examples are: THF for tetrahydrofuran; DMF for N,N-dimethylformamide; DMSO for dimethylsulfoxide; DEAD for diethyl azodicarboxylate; DIAD for diisopropyl azodicarboxylate; EDC for 1-(3-dimethylaminopropyl)-3-ethylcarbodiimide hydrochloride; LDA for lithium diisopropylamide; TFA for trifluoroacetic acid; DMSO for dimethylsulfoxide; DMAP for 4-(N,N-dimethylamino) pyridine; HATU for O-(azabenzotriazole-1-yl)-N,N,N',N'-tetramethyluroniumhexafluorophosphate; Boc for tert-butylcarbonyloxy; DPPA for diphenylphosphoryl azide; DCC for dicyclohexylcarbodiimide; HOOBT for 3-hydroxy-1,2,3-benzotriazin-4(3H)-one; HOBT for 1-hydroxybenzotriazole hydrate; EDCI for 1-(3-dimethylaminopropyl)-3-ethylcarbodiimide hydrochloride; CDI for 1,1'-carbonyldiimidazole; and DMAP for N,N-dimethylaminopyridine.

Scheme 1

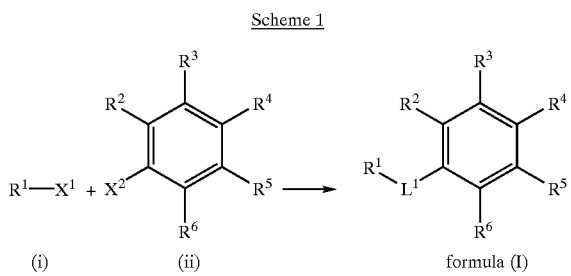

formula (I)

As shown in Scheme 1, the compounds having formula (I) were prepared by reacting intermediate (i) with intermediate (ii), wherein $X^1$ and $X^2$ together are $L^1$. With either (i) or (ii), $X^1$ or $X^2$ can be any conventional activated sulfonic acid, examples of which include sulfonyl halides, sulfonic acid anhydrides, and N-sulfonylimidazolides, preferably sulfonyl halides. Although the solvent used in the coupling reactions is not particularly limited, a solvent in which the starting materials are both soluble and which is little reactive with the materials is preferably used. Examples of such solvents are pyridine, triethylamine, THF, dioxane, benzene, toluene, diethyl ether, dichloromethane, DMF, DMSO, or mixtures thereof. When an acid is liberated with the progress of a reaction, such as when using a halide derivative of a sulfonic acid and an amine or alcohol, it is preferable that the reaction is carried out in the presence of a suitable deacidifying agent. For this reason, the use of a basic solvent such as pyridine or triethylamine is particularly preferred, although the reaction can be run in any of the aforementioned solvents with at least a stoichiometric amount of basic solvent present. Although the reactions generally proceed at room temperature, they can be run at lower or elevated temperatures, as needed. The reaction time is generally 30 minutes to 18 hours and can be arbitrarily selected depending on the types of starting materials and reaction temperature. When the product has a protected amino or hydroxyl group, the product, if necessary, can be converted to a compound having formula (I) having a free amino or hydroxyl group by a conventional deprotection method such as treatment with acid, piperidine, or catalytic hydrogenation in the presence of a catalyst such as palladium on carbon. When the compound having formula (I) has a nitro group, the nitro group can also be reduced. Although the reduction can be conducted by any conventional process, the conversion of a nitro group to an amine is preferably conducted by catalytic hydrogenation using palladium on carbon or platinum oxide as the catalyst or reduction using an acid together with zinc, iron, or tin. The catalytic reduction is conducted in an organic solvent such as methanol, ethanol, or THF under normal or elevated temperature. Groups on the compounds having formula (I) having endogenous or exogenous amino groups can optionally alkylated, formylated, acetylated or otherwise reacted with any number of amine-derivatization reagents well-known to those of ordinary skill in the art. For example, acidic N—H groups can be reacted with alcohols under Mitsunobu conditions. Preferable Mitsunobu conditions include reacting the compounds having formula (I) with alcohols in the presence of a phosphine, preferably triphenylphosphine or tri n-butylphosphine and an activating agent such as DEAD or DIAD. Although the solvent to be used in the reaction is not particularly limited, polar, aprotic solvents such as THF or dioxane are particularly preferable for Mitsunobu reactions. The compounds having formula (I) can also be alkylated with any number of reagents well-known to those of ordinary skill in the art. For example, compounds having formula (I) can be reacted with an unsubstituted or substituted alkylating agent in the presence of a non-nucleophilic base such as sodium or potassium hydride or lithium, sodium, or potassium bis(trimethylsilyl) amide. Although the solvent to be used in the reaction is not particularly limited, polar, aprotic solvents such as THF, DMF, DMSO, or dioxane are particularly preferable for alkylation reactions. Compounds having formula (I) can be reacted with halogenation agents. Examples of halogenating agents include N-chlorosuccinamide, N-bromosuccinamide, 1,3-bibromo-5,5-dimethylhydantoin, N-bromoacetamide, bromine, chlorine, or iodine. Although the solvent to be used in the reaction is not particularly limited, chloroalkanes such as dichloromethane, chloroform, or carbon tetrachloride, halogenated aromatic rings such as chlorobenzene and dichlorobenzene, water, or organic acids, such as acetic acid, are particularly preferable.

Scheme 2

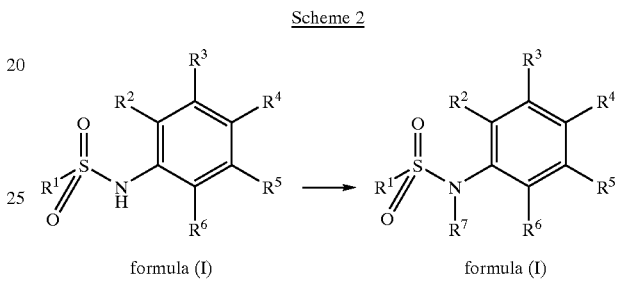

formula (I)                    formula (I)

As shown in Scheme 2, compounds of formula (I) ($R^7$ is H) can be intraconverted to compounds of formula (I) ($R^7$ is an aminoacyl, bisaminoacyl (2-mer), or trisaminoacyl (3-mer) residue optionally capped with a carboxyl protecting group) by reaction with naturally or unnaturally occurring amino acids or with 2-mers and 3-mers derived from amino acids. Representative amino acids include N,N-dimethylglycine, N-methyl-L-proline, N,N-dimethyl-L-valine, N-tert-butoxycarbonyl)-L-valine, N-(tert-butoxycarbonyl)-L-N-methylalanine, (S)-N-(tert-butoxycarbonyl)-2-phenylglycine, N-(tert-butoxycarbonyl)-L-phenylalanine, N-(tert-butoxycarbonyl)-L-proline, N,N-di-(tert-butoxycarbonyl)-L-lysine, N-(tert-butoxycarbonyl)-L-valine, N-(tert-butoxycarbonyl)-L-aspartic acid 1-tert-butyl ester, N-(tert-butoxycarbonyl)-L-aspartic acid 4-tert-butyl ester, N-(tert-butoxycarbonyl)-L-glutamic acid 1-tert-butyl ester, N-(tert-butoxycarbonyl)-L-glutamic acid 5-tert-butyl ester, (bis(2-methoxyethyl)amino)acetic acid, 4-morpholinylacetic acid, (4-methyl-1-piperazinyl)acetic acid, and 4-(((tert-butoxycarbonyl)amino)methyl)benzoic acid in the presence of base and an activating agent. Naturally occurring amino acids can be purchased commercially, while unnaturally occurring amino acids can be synthesized by methods well-known in the art. Representative bases include 4-pyrrolidinylpyridine, DMAP, and triethylamine. Examples of activating used in these reactions include DCC, EDCI, HOBT, and CDI. Typical solvents used in these reactions include dichloromethane, carbon tetrachloride, and chloroform. The reaction temperature is about 0° C. to about 30° C. and depends on the method chosen. Reaction times are typically about 2 to about 24 hours. In a preferred embodiment, compounds of formula (I) (R is H) in dichloromethane at room temperature are reacted with a naturally or unnaturally occurring amino acid in the presence of DCC and 4-pyrrolidinylpyridine for 16 hours to provide compounds of formula (I) ($R^7$ is an aminoacyl, bisaminoacyl (2-mer), or trisaminoacyl (3-mer) residue optionally capped with a carboxyl protecting group).

Scheme 3

Scheme 3 shows the method of preparation for compounds of formula (I) ($L^1$ is —S(O)$CR^{12}R^{13}$—, —$SO_2CR^{12}R^{13}$—, —$SCR^{12}R^{13}$—, —$CR^{12}R^{13}S(O)$—, —$CR^{12}R^{13}SO_2$—, or —$CR^{12}R^{13}S$—). Intermediates (iii) and (iv) (one of $A^1$ and $A^2$ is —$CH_2Cl$; the other is SH) can be combined in the presence of base to provide the desired products. Examples of bases used in these reactions include KOH, NaOH, and LiOH. Representative solvents include N,N-dimethylformamide, dioxane, N-methylpyrrolidinone, and mixtures thereof. The reaction temperature is about 25° C. to about 50° C. and reaction times are typically about 1 to about 12 hours.

Compounds of formula (I) ($L^1$ is —$SCR^{12}R^{13}$— or —$CR^{12}R^{13}S$—) can be intraconverted to compounds of formula (I) ($L^1$ is S(O)$CR^{12}R^{13}$—, —$SO_2CR^{12}R^{13}$—, —$SCR^{12}R^{13}$—, —$CR^{12}R^{13}S(O)$—, or —$CR^{12}R^{13}SO_2$—) by treatement with an oxidizing agent. Representative oxidizing agents include $H_2O_2$ with acetic anhydride, and potassium peroxymonosulfate (OXONE®). Examples of solvents used in these reactions include dichloromethane, acetone, 1,2-dichloroethane, chloroform, and mixtures thereof. The reaction temperature is about 25° C. to about 40° C. and depends on the method chosen. Reaction times are typically about 8 hours to about 24 hours.

Compounds of formula (I) wherein $L^1$ is —$SO_2CR^{12}R^{13}$— or —$CR^{12}R^{13}SO_2$— ($R^{12}$ and $R^{13}$ are hydrogen) can be intraconverted to compounds of formula (I) wherein $L^1$ is —$SO_2CR^{12}R^{13}$— or —$CR^{12}R^{13}SO_2$— ($R^{12}$ and $R^{13}$ are alkyl) by treatment with a base and an alkylating agent. Representative bases include lithium hexamethyldisilazide, sodium hexamethyldisilazide, potassium hexamethyldisilazide, and lithium diisopropylamide. Representative alkylating agents include iodomethane, bromopropane, iodobutane, and the like. Examples of solvents used in these reactions include tetrahydrofuran, dioxane, diethyl ether, and methyl tert butyl ether. Reaction times are about 2 hours to about 6 hours, and reaction temperatures are typically about 0° C. to about 30° C.

The compounds and processes of the present invention will be better understood in connection with the following examples, which are intended as an illustration of, and not a limitation upon, the scope of the invention as defined in the appended claims.

EXAMPLE 1

4-methoxy-N-(3,4,5-trimethoxyphenyl)benzenesulfonamide

A solution of 3,4,5-trimethoxyaniline (500 mg, 2.8 mmol) in pyridine (5 mL) was treated with 4-methoxybenzenesulfonyl chloride (564 mg, 2.8 mmol) in THF (5 mL), stirred at room temperature for 18 hours, concentrated, redissolved in THF (1 mL), treated with water with stirring, and filtered to provide 820 mg of the desired product.

MS (DCI/$NH_3$) m/z 354 (M+H)$^+$ and 371 (M+$NH_4$)$^+$;
$^1$H NMR (300 MHz, $CDCl_3$) δ7.85 (d, J=7.5 Hz, 2H), 6.91 (d, J=7.5 Hz, 2H), 6.29 (s, 2H), 3.84 (s, 3H), 3.78 (s, 3H), 3.75 (s, 6H).

EXAMPLE 2

3,4-dimethoxy-N-(3,4,5-trimethoxyphenyl)benzamide 3,4,5-trimethoxyaniline (232 mg) was processed as described in Example 1 (substituting 3,4-dimethoxybenzenesulfonyl chloride for 4-methoxybenzenesulfonyl chloride with) to provide 375 mg of the desired product.

MS (DCI/$NH_3$) m/z 384 (M+H)$^+$ and 401 (M+$NH_4$)$^+$;
$^1$H NMR (300 MHz, $CDCl_3$) δ7.38 (dd, J=2.4, 8.4 Hz, 1H), 7.18 (d, J=2.4 Hz, 1H), 6.87 (d, J=8.4 Hz, 1H), 6.30 (s, 2H), 3.92 (s, 3H), 3.82 (s, 3H), 3.79 (s, 3H), 3.76 (s, 6H).

EXAMPLE 3

4-trifluoromethoxy-N-(3,4,5-trimethoxyphenyl)benzenesulfonamide 3,4,5-trimethoxyaniline (200 mg) was processed as described in Example 1 (substituting 4-trifluoromethoxybenzenesulfonyl chloride for 4-methoxybenzenesulfonyl chloride with) to provide 330 mg of the desired product.

MS (DCI/$NH_3$) m/z 408 (M+H)$^+$ and 425 (M+$NH_4$)$^+$;
$^1$H NMR (DMSO-$d_6$, 300 MHz) δ10.05 (s, 1H), 7.08 (d, J=9.3 Hz, 1H), 6.98 (s, 2H), 6.86 (d, J=9.3 Hz, 1H), 3.76 (s, 6H), 3.70 (s, 3H), 3.64 (s, 3H).

EXAMPLE 4

4-trifluoromethyl-N-(3,4,5-trimethoxyphenyl)benzenesulfonamide 3,4,5-trimethoxyaniline (200 mg) was processed as described in Example 1 (substituting 4-trifluoromethylbenzenesulfonyl chloride for 4-methoxybenzenesulfonyl chloride with) to provide 375 mg of the desired product.

MS (DCI/$NH_3$) m/z 392 (M+H)$^+$ and 409 (M+$NH_4$)$^+$;
$^1$H NMR (DMSO-$d_6$, 300 MHz) δ10.35 (s, 1H), 7.98 (s, 4H), 6.37 (s, 2H), 3.65 (s, 6H), 3.57 (s, 3H).

EXAMPLE 5

4-nitro-N-(3,4,5-trimethoxyphenyl)benzenesulfonamide 3,4,5-trimethoxyaniline (500 mg) was processed as described in Example 1 (substituting 4-nitrobenzenesulfonyl chloride for 4-methoxybenzenesulfonyl chloride) to provide 850 mg of the desired product.

MS (DCI/$NH_3$) m/z 369 (M+H)$^+$ and 386 (M+$NH_4$)$^+$;
$^1$H NMR (DMSO-$d_6$, 300 MHz) δ10.46 (s, 1H), 8.39 (d, J=8.4 Hz, 2H), 8.02 (d, J=8.4 Hz, 2H), 6.39 (s, 2H), 3.66 (s, 6H), 3.56 (s, 3H).

EXAMPLE 6

4-amino-N-(3,4,5-trimethoxyphenyl)benzenesulfonamide

A solution of Example 5 (100 mg, 0.20 mmol) in in 1:1 THF:methanol (2 mL) was purged with nitrogen, treated with and 10% palladium on carbon (100 mg), stirred under hydrogen (1 atm) for 2 hours, filtered through diatomaceous earth (Celite®), and concentrated to provide 90 mg of the desired product.

MS (DCI/NH$_3$) m/z 339 (M+H)$^+$ and 356 (M+NH$_4$)$^+$;

$^1$H NMR (DMSO-d$_6$, 300 MHz) δ9.69 (s, 1H), 7.41 (d, J=8.7 Hz, 2H), 6.54 (d, J=8.7 Hz, 2H), 6.36 (s, 2H), 5.98 (br s, 2H), 3.64 (s, 6H), 3.55 (s, 3H).

EXAMPLE 7

4-((2-chloroacetyl)amino)-N-(3,4,5-trimethoxyphenyl)benzenesulfonamide

A suspension of Example 6 (30 mg, 0.09 mmole) in dichloromethane (1 mL) was treated sequentially with triethylamine (19 µL) and chloroacetic anhydride (46 mg) to form a clear solution, and concentrated to provide diacylated product. The diacylated product was dissolved in methanol (1 mL), treated with NaHCO$_3$, and stirred for 18 hours. The slurry was washed with water, dried (Na$_2$SO$_4$), filtered, and concentrated to provide 15 mg of the desired product.

MS (DCI/NH$_3$) m/z 415 (M+H)$^+$ and 437 (M+Na)$^+$;

$^1$H NMR (DMSO-d$_6$, 300 MHz) δ10.67 (s, 1H), 7.74 (s, 4H), 6.36 (s, 2H), 4.28 (s, 2H), 3.64 (s, 6H), 3.55 (s, 3H).

EXAMPLE 8

2-nitro-N-(3,4,5-trimethoxyphenyl)benzenesulfonamide 3,4,5-trimethoxyaniline (413 mg) was processed as described in Example 1 (substituting 2-nitrobenzenesulfonyl chloride for 4-methoxybenzenesulfonyl chloride) to provide 800 mg of the desired product.

MS (DCI/NH$_3$) m/z 369 (M+H)$^+$ and 386 (M+NH$_4$)$^+$;

$^1$H NMR (DMSO-d$_6$, 300 MHz) δ7.95 (m, 2H), 7.50 (m, 2H), 6.41 (s, 2H), 3.67 (s, 6H), 3.57 (s, 3H).

EXAMPLE 9

4-methoxy-3-nitro-N-(3,4,5-trimethoxyphenyl)benzenesulfonamide

EXAMPLE 9A 4-methoxy-3-nitrobenzenesulfonyl chloride

A solution of 4-methoxy sulfonyl chloride (2 g) in sulfuric acid (8 mL) at 0° C. was treated dropwise with nitric acid, stirred at 0° C. for about 10 minutes, and carefully poured into a separatory funnel containing diethyl ether and ice. The water layer was extracted with diethyl ether (3×), and the combined extracts were dried (Na$_2$SO$_4$), filtered, and concentrated. The concentrate was dissolved into dichloromethane, washed with brine, dried (Na$_2$SO$_4$), filtered, concentrated, placed under high vacuum, and purified by flash column chromatography on silica gel with 4:1 hexane/ethyl acetate to provide the desired product.

EXAMPLE 9B 4-methoxy-3-nitro-N-(3,4,5-trimethoxyphenyl)benzenesulfonamide 3,4,5-trimethoxyaniline (146 mg) was processed as described in Example 1 (substituting Example 9A for 4-methoxybenzenesulfonyl chloride) to provide 280 mg of the desired product.

MS (DCI/NH$_3$) m/z 416 (M+NH$_4$)$^+$;

$^1$H NMR (DMSO-d$_6$, 300 MHz) δ8.26 (d, J=2.1 Hz, 1H), 7.99 (dd, J=2.1, 9 Hz, 1H), 7.53 (d, J=9 Hz, 1H), 6.39 (s, 2H), 3.98 (s, 3H), 3.67 (s, 6H), 3.57 (s, 3H).

EXAMPLE 10

3-amino-4-methoxy-N-(3,4,5-trimethoxyphenyl)benzenesulfonamide hydrochloride

A solution of Example 9B (150 mg, 0.38 mmol) in 1:1 THF:methanol (8 mL) was treated with 10% palladium on carbon (100 mg), stirred under hydrogen (1 atm) for 1 hour, filtered through diatomaceous earth (Celite®), and concentrated. The concentrate was dissolved in methanol (0.5 mL), treated with 1M HCl in diethyl ether to form a white solid, treated with additional diethyl ether to cause the salt to fully precipitate, and filtered. The hydroscopic salt was dissolved in water (2 mL) and lyophilized to provide 100 mg of the desired product.

MS (DCI/NH$_3$) m/z 369 (M+H)$^+$ 386 (M+NH$_4$)$^+$;

$^1$H NMR (DMSO-d$_6$, 300 MHz) δ9.85 (s, 1H), 7.05 (d, J=2.4 Hz, 1H), 6.98 (dd, J=2.4, 8.1 Hz, 1H), 6.88 (d, J=8.1 Hz, 1H), 6.38 (s, 2H), 5.19 (s, 1H), 3.80 (s, 3H), 3.65 (s, 6H), 3.55 (s, 3H).

EXAMPLE 11

1-formyl-N-(3,4,5-trimethoxyphenyl)indoline-5-sulfonamide

EXAMPLE 11A

N-formylindoline

A solution of indoline (5.0 g) and 98% formic acid (3.0 g) in toluene (17 mL) was heated at reflux for 6 hours with a Dean-Stark trap, cooled, washed with water and concentrated. The resulting dark brown solid was dissolved in methanol, concentrated to a fraction of its original volume, treated with 1:1 diethyl ether/hexane, and concentrated dryness to provide 5.5 g of the desired product.

EXAMPLE 11B 5-chlorosulfonylindoline-1-carboxaldehyde

Chlorosulfonic acid (4.6 mL) at 0° C. was treated portionwise with a sample of Example 11A (2.0 g) over 30 minutes, stirred for 5 minutes at 0° C., heated at 100° C. until all bubbling ceased, carefully poured over ice and water, stired vigorously for 2 hours, filtered, and dried overnight in a vacuum oven to provide 2.5 g of the desired product.

EXAMPLE 11C 1-formyl-N-(3,4,5-trimethoxyphenyl)indoline-5-sulfonamide 3,4,5-trimethoxyaniline (2.51 g) was processed as described in Example 1 (substituting Example 11B for 4-methoxybenzenesulfonyl chloride) and purified by column chromatography on silica gel with 2% methanol/dichloromethane to provide 4.8 g of the desired product.

MS (DCI/NH$_3$) 410 (M+NH$_4$)$^+$;

$^1$H NMR (DMSO-d$_6$, 300 MHz) δ9.85 (s, 1H), 7.05 (d, J=2.4 Hz, 1H), 6.98 (dd, J=2.4, 8.1 Hz, 1H), 6.88 (d, J=8.1 Hz, 1H), 6.38 (s, 2H), 5.19 (s, 1H), 3.80 (s, 3H) 3.65 (s, 6H), 3.55 (s, 3H).

EXAMPLE 12

N-(3,4,5-trimethoxyphenyl)indoline-5-sulfonamide

A solution of Example 11C (4.8 g) in methanol (60 mL) at room temperature was treated with HCl gas for about 8 minutes, concentrated to dryness, and treated with ethyl acetate and water. The organic layer was washed with saturated aqueous $NaHCO_3$ until the aqueous washings were slightly basic, dried ($Na_2SO_4$), filtered, and concentrated to provide 4.0 g of the desired product.

MS (DCI/$NH_3$) m/z 365 (M+H)$^+$ 382 (M+$NH_4$)$^{30}$;

$^1$H NMR (DMSO-$d_6$, 300 MHz) δ9.69 (s, 1H), 7.34 (m, 1H), 6.42 (m, 2H), 6.37 (s, 3H), 3.65 (s, 6H), 3.53 (s, 3H), 3.50 (t, J=9 Hz, 2H), 2.94 (t, J=9 Hz, 2H).

EXAMPLE 13

5-nitro-N-(3,4,5-trimethoxyphenyl)-1H-indole-3-sulfonamide

EXAMPLE 13A

5-nitro-1H-indole-3-sulfonyl chloride

A solution of chlorosulfonic acid (3 mL, 45 mmol) and $Na_2SO_4$ (700 mg, 4.9 mmol) in dichloromethane (30 mL) was treated dropwise with a solution of 5-nitroindole (800 mg, 4.9 mmol) in dichloromethane (20 mL) over 1 hour, stirred for another 30 minures, and decanted to provide a thick brown oil. The oil was slowly treated with water (20 mnL), stirred for 10 minutes, filtered, and dried in a vacuum oven to provide 651 mg of the desired product.

EXAMPLE 13B

5-nitro-N-(3,4,5-trimethoxyphenyl)-1H-indole-3-sulfonamide 3,4,5-trimethoxyaniline (100 mg) was processed as described in Example 1 (substituting Example 13A for 4-methoxybenzenesulfonyl chloride) and purified by column chromatography on silica gel with 2% methanol/dichloromethane to provide 120 mg of the desired product.

MS (DCI/$NH_3$) m/z 407 (M+H)$^+$ 425 (M+$NH_4$)$^+$;

$^1$H NMR (DMSO-$d_6$, 300 MHz) δ10.15 (s, 1H), 8.71 (d, J=2.1 Hz, 1H), 8.27 (s, 1H), 8.10 (dd, J=2.1, 9 Hz, 1H), 7.66 (d, J=9 Hz, 1H), 6.38 (s, 2H), 3.60 (s, 6H), 3.50 (s, 3H).

EXAMPLE 14

1-methyl-N-(3,4,5-trimethoxyphenyl)indoline-5-sulfonamide

A solution of Example 11C (300 mg, 0.77 mmol) in THF (15 mL) at room temperature was treated with 1M $LiAlH_4$ (7.7 mL, 7.7 mmol) to form a solid which later dissolved to give a cloudy yellow solution, stirred overnight at room temperature, cooled to 0° C., treated sequentially with water (0.3 mL), 15% NaOH (0.3 mL) and water (0.9 mL), stirred 30 minutes, and filtered to remove the aluminum complex. The layers comprising the filtrate were separated, and the organic layer was treated with ethyl acetate (50 mL), washed with water (2×20 mL), dried ($Na_2SO_4$), filtered and concentrated. The concentrate was purified by flash column chromatography on silica gel with 2% methanol:dichloromethane to provide 260 mg of the desired product.

MS (DCI/$NH_3$) m/z 379 (M+H)$^+$;

$^1$H NMR (DMSO-$d_6$, 300 MHz) δ9.76 (s, 1H), 7.45 (dd, J=2.1, 8.4 Hz, 1H), 7.34 (d, 1H), 6.46 (d, J=8.4 Hz, 1H), 6.37 (s, 2H), 3.65 (s, 6H), 3.55 (s, 3H), 3.42 (t, J=8.4 Hz, 2H) 2.92 (t, J=8.4 Hz, 2H) 2.76 (s, 3H).

EXAMPLE 15

1-methyl-5-nitro-N-(3,4,5-trimethoxyphenyl)-1H-indole-3-sulfonamide

EXAMPLE 15A

1-methyl-5-nitro-1H-indole-3-sulfonyl chloride

A solution of chlorosulfonic acid (1.9 mL, 28 mmol) and $Na_2SO_4$ (403 mg, 2.8 mmol) in dichloromethane (17 mL) was treated with a solution of 1-methyl-5-nitro-1H-indole (500 mg, 2.8 mmol) in dichloromethane (11 mL) over 1 hour, stirred for 30 minutes, and decanted to provide a thick brown oil. The oil was slowly treated with water (20 mL), stirred for 10 minutes, and filtered. The filtrate was dried in a vacuum oven to provide 80 mg of the desired compound which was used in the next step without further purification.

EXAMPLE 15B

1-methyl-5-nitro-N-(3,4,5-trimethoxyphenyl)-1H-indole-3-sulfonamide 3,4,5-trimethoxyaniline (47 mg) was processed as described in Example 1 (substituting Example 15A for 4-methoxybenzenesulfonyl chloride) to provide 59 mg of the desired product.

MS (DCI/$NH_3$) m/z 439 (M+$NH_4$)$^+$;

$^1$H NMR (DMSO-$d_6$, 300 MHz) δ10.20 (s, 1H), 8.71 (d, J=2.1 Hz, 1H), 8.34 (s, 1H), 8.15 (dd, J=2.1, 9 Hz, 1H), 7.76 (d, J=9 Hz, 1H), 6.40 (s, 2H), 3.91 (s, 3H), 3.61 (s, 6H) 3.51 (s, 3H).

EXAMPLE 16

5-amino-1-methyl-N-(3,4,5-trimethoxyphenyl )-1H-indole-3-sulfonamide

A solution of Example 15 (50 mg, 0.12 mmole) in 1:1 methanol:THF (2 mL) was treated with 10% palladium on carbon, stirred under hydrogen (1 atm) for 2.5 hours, filtered through diatomaceous earth (Celite®), concentrated, redissolved in a small amount of methanol, treated with several drops of 1M HCl in diethyl ether until the solution became cloudy and acidic, treated with additional diethyl ether until a solid precipitated, filtered and dried in a vacuum oven to provide 35 mg of the desired the product.

MS (DCI/$NH_3$) m/z 392 (M+H)$^+$ 409 (M+$NH_4$)$^+$;

$^1$H NMR (DMSO-$d_6$, 300 MHz) δ9.88 (s, 1H), 7.82 (s, 1H), 7.20 (d, J=9 Hz, 1H), 6.98 (d, J=2.4 Hz, 1H), 6.64 (dd, J=2.4, 9 Hz, 1H), 6.39 (s, 2H), 3.71 (s, 3H), 3.62 (s, 6H), 3.52 (s, 3H).

EXAMPLE 17

5-amino-N-(3,4,5-trimethoxyphenyl)-1H-indole-3-sulfonamide

Example 13B (100 mg) was processed as described in Example 16 to provide 80 mg of the desired product.

MS (DCI/$NH_3$) m/z 378 (M+H)$^+$ 395 (M+$NH_4$)$^+$;

$^1$H NMR (300 MHz, $CDCl_3$) δ8.10 (d, 1H), 7.83 (m, 1H), 7.60 (d, 1H), 7.26 (m,1H), 6.39 (s, 2H), 3.61 (s, 6H), 3.52 (s, 3H).

EXAMPLE 18

N-(3,4,5-trimethoxyphenyl)-1H-indole-5-sulfonamide

A solution of Example 12 (0.909 g) and salcomine (0.082 g) in methanol (125 mL) was treated with $O_2$ gas over 18 hours and concentrated. The concentrate was purified by flash column chromatography on silica gel with 2% methanol/dichloromethane to provide the desired compound.

MS (DCI/NH$_3$) m/z 363 (M+H)$^+$ 380 (M+NH$_4$)$^+$;

$^1$H NMR (300 MHz, CDCl$_3$) δ9.94 (s, 1H), 8.07 (s, 1H), 7.52 (m, 2H), 6.61 (m,1H), 6.39 (s, 2H), 3.61 (s, 6H), 3.51 (s, 3H).

EXAMPLE 19

1-methyl-N-(3,4,5-trimethoxyphenyl)-1H-indole-5-sulfonamide

A solution of Example 18 (1.01 g, 2.8 mmol) in THF (100 mL) at 0° C. was treated with sodium bis(trimethylsilyl) amide (1M in THF, 7 mL, 6.89 mmol), stirred for 20 minutes, treated dropwise with CH$_3$I (195 μL, 3.1 mmol), stirred over 18 hours while warming to room temperature, treated with water, and extracted with ethyl acetate. The extract was dried (Na$_2$SO$_4$), filtered and concentrated. The concentrate was purified by flash column chromatography on silica gel with 1% methanol/dichloromethane to provide 684 mg of the desired compound.

MS (DCI/NH$_3$) m/z 377 (M+H)$^+$ 394 (M+NH$_4$)$^+$;

$^1$H NMR (DMSO-d$_6$, 300 MHz) δ9.94 (s, 1H), 8.06 (t, 1H), 7.57 (m, 2H), 7.49 (d, J=3.3 Hz, 1H), 6.64 (d, J=3.3 Hz, 1H), 6.39 (s, 1H), 3.81 (s, 3H), 3.62 (s, 6H), 3.51 (s, 3H).

EXAMPLE 20

N,1-dimethyl-N-(3,4,5-trimethoxyphenyl)-1H-indole-5-sulfonamide

A solution of example Example 18 (50 mg, 0.14 mmol) in THF at 0° C. was treated portionwise with NaH (60% dispersion in mineral oil, 26 mg, 0.70 mmol), stired for 20 minutes, treated dropwise with CH$_3$I (52 μL, 0.84 mmol), warmed to room temperature, stirred for 18 hours, treated with water, and extracted with ethyl acetate (10 mL). The organic layer was washed sequentially with water (5 mL) and brine (5 mL), dried (Na$_2$SO$_4$), filtered, and concentrated. The concentrate was purified by flash column chromatography on silica gel with 1% methanol:dichloromethane to provide 48 of the desired product.

MS (DCI/NH$_3$) m/z 391 (M+H)$^+$;

$^1$H NMR (DMSO-d$_6$, 300 MHz) δ7.86 (d, J=1.5 Hz, 1H), 7.64 (d, J=8.4 Hz, 1H), 7.54 (d, J=2.7 Hz, 1H), 7.32 (dd, J=1.5, 8.4 Hz, 1H), 6.65 (d, J=2.7 Hz, 1H), 6.29 (s, 2H), 3.86 (s, 3H), 3.64 (s, 3H), 3.58 (s, 6H), 3.06 (s, 3H).

EXAMPLE 21

3,4,5-trimethoxy-N-(4-methoxyphenyl) benenesulfonamide

EXAMPLE 21A 3,4,5-trimethoxybenzenesulfonyl chloride

The procedure in *J. Het. Chem.* 23, 1253 (1986) was followed. A solution of 3,4,5-trimethoxyaniline (5.0 g) in acetic acid (26 mL) and 12M HCl (47 mL) at −10–5° C. was treated slowly with a solution of NaNO$_2$ (2 g) in water (7 mL), stirred at −5° C. for another 30 minutes, added in portions to a cold (−5° C.) solution of CuCl$_2$ and SO$_2$ in acetic acid (35 mL) and water (6 mL), stirred at −5–0° C. for 3 hours, warmed to room temperature overnight, poured over ice, filtered, and dried to provide the desired product.

EXAMPLE 21B 3,4,5-trimethoxy-N-(4-methoxyphenyl) benenesulfonamide

A solution of 4-methoxyaniline (139 mg, 1.1 mmol) in pyridine (2 mL) was treated with Example 21A (300 mg, 1.1 mmol) in THF (2 mL), stirred at room temperature for 18 hours, concentrated, redissolved in THF (1 mL), treated with water with stirring, and filtered to provide 300 mg of the desired product.

MS (DCI/NH$_3$) m/z 353 (M+H)$^+$ and 371 (M+NH$_4$)$^+$;

$^1$H NMR (300 MHz, CDCl$_3$) δ6.99 (d, J=9 Hz, 1H), 6.80 (d, J=9 Hz, 1H), 6.85 (s, 2H), 3.87 (s, 3H), 3.77 (s, 3H), 3.76 (s, 6H).

EXAMPLE 22

N-(3-hydroxy-4-methoxyphenyl)-3,4,5-trimethoxybenzamide

Example 21A was processed as described in Example 21B (substituting 5-amino-2-methoxyphenol for 4-methoxyaniline) to provide the desired product.

MS (DCI/NH$_3$) m/z 369 (M+H)$^+$ and 387 (M+NH$_4$)$^+$;

$^1$H NMR (300 MHz, CDCl$_3$) δ6.92 (s, 2H), 6.72 (d, J=8.7 Hz, 1H), 6.69 (d, 1H), 6.57 (dd, J=2.7, 8.7 Hz, 1H), 3.87 (s, 3H), 3.85 (s, 3H), 3.78 (s, 6H).

EXAMPLE 23

N-(1-methyl-1H-indol-5-yl)-3,4,5-trimethoxybenzenesulfonamide

Example 21A (456 mg) was processed as described in Example 21B (substituting 1H-indol-5-amine for 4-methoxyaniline) to provide 480 mg of the desired product.

MS (DCI/NH$_3$) m/z 377 (M+H)$^+$ and 394 (M+NH$_4$)$^+$;

$^1$H NMR (300 MHz, CDCl$_3$) δ7.32 (d, J=3 Hz, 1H), 7.19 (d, J=8.4 Hz, 1H), 7.05 (d, J=3 Hz, 1H), 6.90 (dd, J=3.0, 8.4 Hz, 1H), 6.86 (s, 2H), 6.40 (d, J=3 Hz, 1H), 3.85 (s, 3H), 3.76 (s, 3H), 3.68 (s, 6H).

EXAMPLE 24

N-(4-(dimethylamino)phenyl)-3,4,5-trimethoxybenzenesulfonamide

Example 21A (195 mg) was processed as described in Example 21B (substituting N',N'-dimethyl-1,4-benzenediamine for 4-methoxyaniline) to provide 200 mg of the desired product.

MS (DCI/NH$_3$) m/z 367 (M+H)$^+$;

$^1$H NMR (DMSO-d$_6$, 300 MHz) δ9.55 (s, 1H), 6.93 (s, 2H), 6.90 (d, J=9 Hz, 2H), 6.86 (s, 1H), 6.61 (d, J=9 Hz, 2H), 3.75 (s, 3H), 3.74 (s, 6H), 2.81 (s, 6H).

EXAMPLE 25

N-(4-fluoro-3-methoxyphenyl)-3,4,5-trimethoxybenzenesulfonamide

Example 21A (250 mg) was processed as described in Example 21B (substituting 3-fluoro-4-methoxyaniline for 4-methoxyaniline) to provide 310 mg of the desired product.

MS (DCI/NH$_3$) m/z 371 (M+H)$^+$ and 389 (M+NH$_4$)$^+$;

$^1$H NMR (DMSO-d$_6$, 300 MHz) δ10.05 (s, 1H), 7.08 (d, J=9.3 Hz, 1H), 6.98 (s, 2H), 6.86 (d, J=9.3 Hz, 1H), 3.76 (s, 6H), 3.70 (s, 3H), 3.64 (s, 3H).

EXAMPLE 26

3,4,5-trimethoxy-N-(4-(trifluoromethoxy)phenyl)benzenesulfonamide

Example 21A (125 mg) was processed as described in Example 21B (substituting 4-trifluoromethoxyaniline for 4-methoxyaniline) to provide 125 mg of the desired product.

MS (DCI/NH$_3$) m/z 407 (M+H)$^+$ and 425 (M+NH$_4$)$^+$;

$^1$H NMR (DMSO-d$^6$, 300 MHz) δ10.37 (s, 1H), 7.29 (d, J=9.3 Hz, 2H), 7.21 (d, J=9.3 Hz, 2H), 6.99 (s, 2H), 3.75 (s, 6H), 3.69 (s, 3H).

EXAMPLE 27

3,4,5-trimethoxy-N-(2,3,4,5,6-pentafluorophenyl)benzenesulfonamide

Example 21A (125 mg) was processed as described in Example 21B (substituting 2,3,4,5,6-pentafluoroaniline for 4-methoxyaniline) to provide 120 mg of the desired product.

MS (DCI/NH$_3$) m/z 413 (M+H)$^+$ and 431 (M+NH$_4$)$^+$;

$^1$H NMR (DMSO-d$_6$, 300 MHz) δ7.02 (s, 2H), 3.81 (s, 3H), 3.79 (s, 6H).

EXAMPLE 28

N-(3-amino-4-methoxyphenyl)-3,4,5-trimethoxybenzenesulfonamide hydrochloride

EXAMPLE 28A tert-butyl 2-methoxy-5-nitrophenylcarbamate

A solution of 2-methoxy-5-nitroaniline (2.0 g, 12 mmol) in dichloromethane was treated sequentially with NaHCO$_3$ and di(tert-butyl)dicarbonate, stirred at room temperature overnight, treated with DMAP (10 mgs) and triethylamine (600 μL, 4 mmol), stirred at room temperature for 2 days, neutralized with 1M HCl, and extracted with ethyl acetate (500 mL). The organic layer was dried (Na$_2$SO$_4$), filtered, and concentrated. The concentrate was purified by flash chromatography on silica gel with 5% methanol:dichloromethane to provide 3 g of the desired product.

EXAMPLE 28B tert-butyl 5-amino-2-methoxyphenylcarbamate

A solution of Example 28A in 1:1 THF:methanol (40 mL) was treated with 10% palladium on carbon (800 mg), stirred under hydrogen (1 atm) for one hour, filtered through diatomaceous earth (Celite®), and concentrated to provide the desired product.

EXAMPLE 28C

N-(3-tert-butoxycarbonylamino-4-methoxyphenyl)-3,4,5-trimethoxybenzenesulfonamide Example 21A (200 mg) was processed as described in Example 21B (substituting Example 28B for 4-methoxyaniline) to provide 300 mg of the desired product.

EXAMPLE 28D

N-(3-amino-4-methoxyphenyl)-3,4,5-trimethoxybenzenesulfonamide hydrochloride

A solution of Example 28C in dichloromethane (1 mL) was treated with 4.0 M HCl in dioxane, stirred for 1 hour, concentrated to a fraction of its original volume, and treated with diethyl ether to precipitate 250 mg of the desired product.

MS (DCI/NH$_3$) m/z 369 (M+H)$^+$ and 386 (M+NH$_4$)$^+$;

$^1$H NMR (DMSO-d$_6$, 300 MHz) δ10.01 (s, 1H), 7.03 (d, 1H), 7.00 (s, 2H), 6.97 (d, 1H), 6.94 (s, 1H), 3.77 (s, 6H), 3.70 (s, 3H).

EXAMPLE 29

3,4,5-trimethoxy-N-(1-methyl-1H-indol-4-yl)benzenesulfonamide

EXAMPLE 29A 1-methyl-4-nitro-1H-indole

A solution of 4-nitroindole (500 mg, 3.1 mmol) in THF (15 mL) at 0° C. was treated portionwise with NaH (290 mg, 9.3 mmol), stirred for 30 minutes, treated dropwise with methyl iodide (0.95 mL, 15.5 mmol), warmed to room temperature for 18 hours, treated sequentially with water and ethyl acetate (200 mL), and washed with brine (100 mL). The organic layer was dried (Na$_2$SO$_4$), filtered, and concentrated to provide the desired product, which was used in the next step without further purification.

EXAMPLE 29B 1-methyl-1H-indol-4-amine

Example 29A (500 mg) was processed as described in Example 28B to provide 400 mg of the desired product.

EXAMPLE 29C 3,4,5-trimethoxy-N-(1-methyl-1H-indol-4-yl)benzenesulfonamide

Example 29B (82 mg, 0.56 mmol) was dissolved in pyridine (1 mL), treated portionwise with Example 21A, (150 mg, 0.56 mmol) in THF (1 mL), stirred for 18 hours, concentrated, treated with a small amount of THF to dissolve the concentrate, and treated with water with vigorous stirring. The precipitate was filtered and dried in a vacuum oven to provide 180 mg of the desired product.

MS (DCI/NH$_3$) m/z 377 (M+H)$^+$ and 394 (M+NH$_4$)$^+$;

$^1$H NMR (300 MHz, CDCl$_3$) δ9.93 (s, 1H), 7.20 (d, J=3 Hz, 1H), 7.18 (d, J=6 Hz, 1H), 7.05 (d, J=7.5 Hz, 1H), 6.99 (s, 2H), 6.95 (dd, J=0.6, 7.5 Hz, 1H), 3.71 (s, 3H), 3.68 (s, 6H), 3.64 (s, 3H).

EXAMPLE 30

3,4,5-trimethoxy-N-(1-methyl-1H-indol-6-yl)benzenesulfonamide

Example 21A (150 mg) was processed as described in Example 21B (substituting 1-methyl-1H-indol-6-amine for 4-methoxyaniline) to provide 200 mg of the desired product.

MS (DCI/NH$_3$) m/z 377 (M+H)$^+$ and 394 (M+NH$_4$)$^+$;

$^1$H NMR (DMSO-d$_6$, 300 MHz) δ9.92 (s, 1H), 7.39 (d, J=8.4 Hz, 1H), 7.25 (d, J=3 Hz, 1H), 7.16 (s, 1H), 7.00 (s, 2H), 6.78 (dd, J=1.85, 8.4 Hz, 1H), 6.33 (d, 1H), 3.70 (s, 6H), 3.68 (s, 3H), 3.66 (s, 3H).

EXAMPLE 31

N-(1H-indol-5-yl)-3,4,5-trimethoxybenzenesulfonamide

Example 21A (100 mg) was processed as described in Example 21B (substituting 1H-indol-5-amine for 4-methoxyaniline) to provide 110 mg of the desired product.

MS (DCI/NH$_3$) m/z 363 (M+H)$^+$ and 380 (M+NH$_4$)$^+$;
$^1$H NMR (DMSO-d$_6$, 300 MHz) δ11.06 (s, 1H), 9.72 (s, 1H), 7.31 (t, J=2.7 Hz, 1H), 7.26 (d, J=1.8 Hz, 1H), 7.24 (s, 1H), 6.95 (s, 2H), 6.85 (dd, J=1.8, 8.7 Hz, 1H), 6.35 (t, J=2.7 Hz, 1H), 3.69 (s, 6H), 3.66 (s, 3H).

EXAMPLE 32

N-(1,2-dimethyl-1H-indol-5-yl)-3,4,5-trimethoxybenzenesulfonamide

EXAMPLE 32A 1,2-dimethyl-1H-indol-5-amine

A solution of 1,2-dimethyl-5-nitro-1H-indole (500 mg) in 1:1 THF:methanol (10 mL) was treated with 10% palladium on carbon (100 mg), stirred under hydrogen (1 atm) for 1 hour, filtered through diatomaceous earth (Celite®), and concentrated. The crude product was used without further purification in the next step.

EXAMPLE 32B

N-(1,2-dimethyl-1H-indol-5-yl)-3,4,5-trimethoxybenzenesulfonamide

Example 21A (100 mg) was processed as described in Example 23B (substituting Example 32A for 4-methoxyaniline) to provide 115 mg of the desired product.
MS (DCI/NH$_3$) m/z 391 (M+H)$^+$ and 408 (M+NH$_4$)$^+$;
$^1$H NMR (DMSO-d$_6$, 300 MHz) δ9.71 (s, 1H), 7.23 (d, J=9 Hz, 1H), 7.15 (d, J=1.8 Hz, 1H), 6.96 (s, 2H), 6.82 (dd, J=1.8, 9 Hz, 1H), 6.12 (s, 1H), 3.70 (s, 6H), 3.66 (s, 3H), 3.58 (s, 3H), 2.34 (s, 3H).

EXAMPLE 33

N-(3-chloro-1H-indol-5-yl)-3,4,5-trimethoxybenzenesulfonamide

A solution of Example 31 (51 mg, 0.14 mmol) in dichloromethane (1.5 mL) and DMF (50 μL) was treated with N-chlorosuccinimide (21 mg, 0.15 mmol), stirred for 2 hours, and treated sequentially with water (1 mL) and ethyl acetate (10 mL). The organic layer was washed sequentially with 0.2 MHCl (5 mL) and saturated aqueous NaHCO$_3$ (5 mL), dried (Na$_2$SO$_4$), filtered, and concentrated to provide 25 mg of the desired product.
MS (DCI/NH$_3$) 414 (M+NH$_4$)$^+$;
$^1$H NMR (DMSO-d$_6$, 300 MHz) δ9.88 (s, 1H), 7.49 (d, 1H), 7.32 (s, 1H), 7.29 (s, 1H), 7.18 (d, J=1.8 Hz, 1H), 6.97 (s, 2H), 6.94 (d, J=1.8 Hz, 1H), 3.70 (s, 6H), 3.67 (s, 3H).

EXAMPLE 34

N-(1H-indazol-5-yl)-3,4,5-trimethoxybenzenesulfonamide

Example 21A (100 mg) was processed as described in Example 21B (substituting 1H-indazol-5-amine for 4-methoxyaniline) to provide 110 mg of the desired product.
MS (DCI/NH$_3$) m/z 364 (M+H)$^+$ and 381 (M+NH$_4$)$^+$;
$^1$H NMR (DMSO-d$_6$, 300 MHz) δ13.02 (s, 1H), 9.95 (s, 1H), 8.00 (s, 1H), 7.45 (d, J=2.1 Hz, 1H), 7.42 (s, 1H), 7.11 (dd, J=2.1, 8.7 Hz, 1H), 6.95 (s, 2H), 3.69 (s, 6H), 3.66 (s, 3H).

EXAMPLE 35

3.4,5-trimethoxy-N-(1-methyl-1H-benzimidazol-6-yl)benzenesulfonamide

5-Nitrobenzimidazole (500 mg) was processed as described for 4-nitroindole in Examples 29A, 29B, and 29C to provide both methylated isomers. The isomers were separated by flash column chromatography on silica gel with 1% methanol:dichloromethane to provide 133 mg of the desired compound as the less polar isomer.
MS (DCI/NH$_3$) m/z 378 (M+H)$^+$;
$^1$H NMR (DMSO-d$_6$, 300 MHz) δ10.08 (s, 1H), 8.10 (s, 1H), 7.50 (d, J=8.4 Hz, 1H), 7.30 (d, J=1.8 Hz, 1H), 7.01 (s, 2H), 6.93 (dd, J=1.8, 8.4 Hz, 1H), 3.75 (s, 3H), 3.71 (s, 6H), 3.67 (s, 3H).

EXAMPLE 36

3.4,5-trimethoxy-N-(1-methyl-1H-benzimidazol-5-yl)benzenesulfonamide

5-Nitrobenzimidazole (500 mg) was processed as described in Example 35 to provide 167 mg of the desired compound as the more polar isomer.
MS (DCI/NH$_3$) m/z 378 (M+H)$^+$;
$^1$H NMR (DMSO-d$_6$, 300 MHz) δ9.98 (s, 1H), 8.13 (s, 1H), 7.44 (d, J=8.7 Hz, 1H), 7.35 (d, J=1.8 Hz, 1H), 7.05 (dd, J=1.8, 8.7 Hz, 1H), 6.99 (s, 2H), 3.77 (s, 3H), 3.71 (s, 6H), 3.66 (s, 3H).

EXAMPLE 37

3,4,5-trimethoxy-N-methyl-N-(1-methyl-1H-indol-5-yl)benzenesulfonamide

A solution of Example 23 (50 mg, 0.13 mmol) in THF (1 mL) at 0° C. was treated with NaH (60% suspension in mineral oil, 15 mg, 0.39 mmol) in portions, stirred at 0° C. for 30 minutes, treated dropwise with methyl iodide (42 μL, 0.65 mmol warmed to room temperature overnight. The product was absorbed on silica gel and purified by flash column chromatography using 1% Methanol:Dichloromethane as the eluent. This afforded the product as a solid (35 mg, 68%) plus some unreacted starting material.
MS (DCI/N$_3$) m/z 391 (M+H)$^+$ and 408 (M+NH$_4$)$^+$;
$^1$H NMR (DMSO-d$_6$, 300 MHz) δ7.40 (d, J=8.7 Hz, 1H), 7.37 (d, J=3 Hz, 1H), 7.25 (d, J=2.1 Hz, 1H), 6.87 (dd, J=2.1, 8.7 Hz, 1H), 6.68 (s, 2H), 6.27 (d, J=8.1 Hz, 1H), 4.03 (s, 3H), 3.75 (s, 3H), 3.73 (s, 6H).

EXAMPLE 38

3,4,5-trimethoxy-N-(2-(dimethylamino)ethyl)-N-(1-methyl-1H-indol-5-yl)benzenesulfonamide A solution of Example 23 (50 mg, 0.13 mmol) in THF (2 mL) was treated sequentially with triphenylphosphine (52 mh, 0.19 mmol), N,N-dimethyl-2-aminoethanol (17 μL, 0.16 mmol), and diethylazodicarboxylate (31 μL, 0.19 mmol), stirred at room temperature overnight, treated with silica gel, and concentrated. The mixture was purified by flash column chromatography on silica gel with 1% methanol:dichloromethane to provide 46 mg of the desired product.
MS (DCI/NH$_3$) m/z 448 (M+H)$^+$ and 470 (M+Na)$^+$;
$^1$H NMR (300 MHz, CDCl$_3$) δ7.40 (d, J=8.7 Hz, 1H), 7.38 (d, J=3 Hz, 1H), 7.26 (d, J=2.1 Hz, 1H), 6.83 (dd, J=2.1, 8.7 Hz, 1H), 6.79 (s, 2H), 6.41 (d, J=3 Hz, 1H), 3.78 (s, 3H), 3.75 (s, 3H), 3.70 (s, 6H), 3.64 (t, 2H), 2.22 (t, 2H) 2.08 (s, 6H).

EXAMPLE 39

1H-indol-5-ol, (3,4,5-trimethoxybenzenesulfonate) ester

A solution of 5-hydroxyindole (CAS number 13523-92-7, 253 mg, 1.9 mmol) in dichloromethane (15 mL) and pyridine (0.5 mL) was treated sequentially with Example 21A (507 mg, 1.9 mmol) and a catalytic amount of DMAP, stirred for 1 week, and washed with saturated $CuSO_4$. The organic layer was dried ($MgSO_4$), filtered, and concentrated. Chromatography of the concentrate on silica gel with 30% ethyl acetate/hexane provided 520 mg of the desired compound as a white crystalline solid.

MS (ESI/$NH_3$) m/z 364 (M+H)$^+$;

$^1$H NMR (300 MHz, $CDCl_3$) δ8.24 (br s, 1H), 7.29–7.25 (m, 3H), 7.02 (s, 2H), 6.82 (dd, J=2.2, 8.8, 1H), 6.51 (m, 1H), 3.92 (s, 3H), 3.78 (s, 6H).

EXAMPLE 40

(3,4,5-trimethoxyphenyl) 4-methoxybenzenesulfonate 3,4,5-trimethoxyphenol (504 mg) was processed as described in Example 43 (substituting 4-methoxybenzenesulfonyl chloride for 4-methoxymetanilyl fluoride) to provide 500 mg of the desired product.

MS (ESI/$NH_3$) m/z 355 (M+H)$^+$;

$^1$H NMR (300 MHz, $CDCl_3$) δ7.81–7.77 (m, 2H), 7.01–6.98 (m, 2H), 6.20 (s, 2H), 3.89 (s, 3H), 3.80 (s, 3H), 3.72 (s, 6H).

EXAMPLE 41

(3,4,5-trimethoxyphenyl) 4-methylbenzenesulfonate 3,4,5-trimethoxyphenol (497 mg) was processed as described in Example 43 (substituting para-toluenesulfonyl chloride for 4-methoxymetanilyl fluoride) to provide 770 mg of the desired product.

MS (ESI/$NH_3$) m/z 339 (M+H)$^+$;

$^1$H NMR (300 MHz, $CDCl_3$) δ7.75 (d, J=8.5, 2H), 7.34 (d, J=8.1, 2H), 6.19 (s, 2H), 3.80 (s, 3H), 3.70 (s, 6H), 2.46 (s, 3H).

EXAMPLE 42

1H-indol-5-yl 3,4,5-trimethoxybenzenesulfonate

Example 21A (726 mg) was processed as described in Example 39 (substituting 1-methyl-1H-indol-5-ol for 5-hydroxyindole to provide 650 mg of the desired product.

MS (ESI/$NH_3$) m/z 395 (M+$NH_4$)$^+$;

$^1$H NMR (300 MHz, $CDCl_3$) δ7.24 (d, J=2.4, 1H), 7.19 (d, J=8.8, 1H), 7.09 (d, J=3.1, 1H), 7.02 (s, 2H), 6.85 (dd, J=2.4, 8.8, 1H), 6.43 (dd, J=0.7, 3.1, 1H), 3.92 (s, 3H), 3.79 (s, 6H), 3.77 (s, 3H).

EXAMPLE 43

(3,4,5-trimethoxyphenyl) 3-amino-4-methoxybenzenesulfonate

A solution of 3,4,5-trimethoxyphenol (505.7 mg, 2.75 mmol) in dichloromethane (28 mL) was treated sequentially with triethylamine (1.2 mL), 4-methoxymetanilyl fluoride (572.5 mg, 2.75 mmol), and tert-butylammonium iodide (106 mg, 0.287 mmol), stirred overnight, and washed once with 1M $Na_2CO_3$. The organic layer was separated, dried ($MgSO_4$), filtered, and concentrated. Chromatography of the concentrate on silica gel with 40% ethyl acetate/hexanes provided 356 mg of the desired compound.

MS (ESI/$NH_3$) m/z 370 (M+H)$^+$;

$^1$H NMR (300 MHz, $CDCl_3$) δ7.25–7.20 (m, 2H). 6.84 (d, J=8.5, 1H), 6.23 (s, 2H), 3.93 (s, 3H), 3.75 (s, 3H), 3.73 (s, 6H).

EXAMPLE 44

(3,4,5-trimethoxyphenyl)-4-(dimethylamino)benzenesulfonate 4-(Dimethylamino)benzenesulfonyl chloride (prepared as described in *J. Am. Chem. Soc.* 1997, 99:3, 851–858, 1.93 g) was processed as described for 4-methoxymetanilyl fluoride in Example 43 to provide 2.55 g of the desired product.

MS (ESI/$NH_3$) m/z 368 (M+H)$^+$;

$^1$H NMR (300 MHz, $CDCl_3$) δ7.66 (d, J=8.8, 2H), 6.66 (d, J=9.2, 2H), 6.22 (s, 2H), 3.79 (s, 3H), 3.71 (s, 6H), 3.07 (s, 6H).

EXAMPLE 45

4-methylphenyl 3,4,5-trimethoxybenzenesulfonate

Example 21A (103 mg) was processed as described in Example 39 (substituting 4-methylphenol for 5-hydroxyindole to provide 26.6 mg of the desired product.

MS (ESI/$NH_3$) m/z 356 (M+$NH_4$)$^+$;

$^1$H NMR (300 MHz, $CDCl_3$) δ7.11–7.08 (m, 2H), 7.01 (s, 2H), 6.90–6.87 (m, 2H), 3.92 (s, 3H), 3.83 (s, 6H), 2.32 (s, 3H).

EXAMPLE 46

3,4,5-trimethoxyphenyl 1-methyl-5-indolinesulfonate

EXAMPLE 46A 1-methyl-5-indolinesulfonyl chloride

A solution of chlorosulfonic acid at 0° C. (5 mL, 75 mmol) was treated portionwise with 1-methylindoline (CAS No. [824-21-5], 1.96 g, 14.7 mmol), warmed to room temperature, heated at 75° C. for 40 minutes, cooled, and poured onto ice to provide a solid. The solid was collected by suction filtration, washed with water, and dried to provide 927 mg of the desired product.

$^1$H NMR (300 MHz, $CDCl_3$) 7.33 (dd, J=1.8, 7.7, 1H), 7.19 (d, J=7.7, 1H), 6.93 (d, J=1.8, 1H), 3.51 (t, J=8.5, 2H), 3.07 (t, J=8.5, 2H), 2.86 (s, 3H).

EXAMPLE 46B 3,4,5-trimethoxyphenyl 1-methyl-5-indolinesulfonate 3,4,5-trimethoxyphenol (103 mg) was processed as described in Example 43 (substituting Example 52A for 4-methoxymetanilyl fluoride) to provide 22 mg of the desired product.

MS (ESI/$NH_3$) m/z 380 (M+H)$^+$;

$^1$H NMR (300 MHz, $CDCl_3$) δ7.12 (s, 2H), 6.79 (s, 1H), 6.24 (s, 2H), 3.80 (s, 3H), 3.72 (s, 6H), 3.46 (t, 2H), 3.02 (t, 2H), 2.77 (s, 3H).

EXAMPLE 47

4-methoxyphenyl 3,4,5-trimethoxybenzenesulfonate

Example 21A (104 mg) was processed as described in Example 39 (substituting 4-methoxyphenol for 5-hydroxyindole to provide 69.6 mg of the desired product.

MS (ESI/NH$_3$) m/z 372 (M+NH$_4$)$^+$;
$^1$H NMR (300 MHz, CDCl$_3$) δ7.00 (s, 2H), 6.93–6.89 (m, 2H), 6.82–6.78 (m, 2H), 3.92 (s, 3H), 3.83 (s, 6H), 3.68 (s, 3H).

EXAMPLE 48 tert-butyl 2-((1-methyl-1H-indol-5-yl)((3,4,5-trimethoxyphenyl)sulfonyl)amino)ethylcarbamate Example 23 (50 mg) was processed as described in Example 38 (substituting N-(tert-butoxycarbonyl) ethanolamine for N,N-dimethyl-2-aminoethanol) to provide 60 mg of the desired product.

MS (DCI/NH$_3$) m/z 520 (M+H)$^+$ and 537 (M+NH$_4$)$^+$;
$^1$H NMR (300 MHz, DMSO-d$_6$) δ7.40 (d, 1H), 7.38 (d, J=3 Hz, 1H), 7.28 (d, 1H), 6.83 (m, 1H), 6.76 (s, 2H), 6.40 (d, J=3 Hz, 1H), 3.79 (s, 3H), 3.75 (s, 3H), 3.71 (s, 6H), 3.57 (s, 2H), 3.16 (d, 1H), 2.96 (q, 2H), 1.32 (s, 9H).

EXAMPLE 49

N-(2-hydroxyethyl)-3,4,5-trimethoxy-N-(1-methyl-1H-indol-5-yl)benzenesulfonamide Example 23 (50 mg) was processed as described in Example 38 (substituting ethylene glycol for N,N-dimethyl-2-aminoethanol) to provide 60 mg of the desired product.

MS (DCI/NH$_3$) m/z 420 (M+H)$^+$;
$^1$H NMR (300 MHz, DMSO-d$_6$) δ8.97 (s, 1H), 7.28 (d, J=2.7 Hz, 1H), 7.26 (d, J=2.1 Hz, 1H), 6.96 (s, 2H), 6.90 (dd, J=8.4 Hz, 2.1 Hz, 1H), 6.34 (d, J=2.7 Hz, 1H), 4.03 (q, J=6.9 Hz, 2H), 3.72 (s, 3H), 3.69 (s, 3H), 3.66 (s, 6H), 1.17 (t, J=6.9 Hz, 2H).

EXAMPLE 50

N-(2,3-dihydro-1,4-benzodioxin-6-yl)-3,4,5-trimethoxybenzenesulfonamide

Example 21A (500 mg) was processed as described in Example 21B (substituting 1,4-benzodioxane-6-amine for 4-methoxyaniline) to provide 651 mg of the desired product.

MS (DCI/NH$_3$) m/z 381 (M+H)$^+$ and 399 (M+NH$_4$)$^+$;
$^1$H NMR (300 MHz, DMSO-d$_6$) δ9.85 (s, 1H), 6.97 (s, 2H), 6.73 (d, 1H), 6.57 (m, 2H), 4.16 (s, 2H), 3.76 (s, 6H), 3.70 (s, 3H).

EXAMPLE 51

N-(2-aminoethyl)-3,4,5-trimethoxy-N-(1-methyl-1H-indol-5-yl)benzenesulfonamide hydrochloride

EXAMPLE 51A benzyl 2-((1-methyl-1H-indol-5-yl)((3,4,5-trimethoxyphenyl)sulfonyl)amino)ethylcarbamate Example 23 (50 mg) was processed as described in Example 38 (substituting benzyl N-(2-hydroxyethyl) carbamate for N,N-dimethyl-2-aminoethanol) to provide 46 mg of the desired product.

EXAMPLE 51B

N-(2-aminoethyl)-3,4,5-trimethoxy-N-(1-methyl-1H-indol-5-yl)benzenesulfonamide

A solution of Example 51A in methanol:THF (1 mL:1 mL) was treated with 10% palladium on carbon (30 mg), stirred under with hydrogen (1 atm) for 2 hours, filtered through diatomaceous earth (Celite®), and concentrated to provide the desired compound.

EXAMPLE 51C

N-(2-aminoethyl)-3,4,5-trimethoxy-N-(1-methyl-1H-indol-5-yl)benzenesulfonamide hydrochloride Example 51B, in less than 1 mL of methanol, was treated with several drops of 1M HCl in diethyl ether to provide a cloudy, acidic solution. Diethyl ether was added to cause precipitation. The precipitate was filtered and oven dried to provide 20 mg of the desired product.

MS (DCl/NH$_3$) m/z 420 (M+H)$^+$;
$^1$H NMR (300 MHz, DMSO-d6) δ7.41 (d, J=8.7 Hz, 1H), 7.38 (d, J=3 Hz, 1H), 7.28 (d, J=2.1 Hz, 1H), 6.83 (dd, J=8.7 Hz, 2.1 Hz, 1H), 6.77 (s, 2H), 6.41 (d, J=3 Hz, 1H), 3.79 (s, 3H), 3.76 (s, 3H), 3.70 (s, 6H).

EXAMPLE 52

3-amino-4-methoxy-N-methyl-N-(3,4,5-trimethoxyphenyl)benzenesulfonamide

EXAMPLE 52A 4-methoxy-N-methyl-3-nitro-N-(3,4,5-trimethoxyphenyl)benzenesulfonamide A solution of Example 9B (100 mg, 0.25 mmol) in THF (2 mL) at ° C. was treated with sodium hydride (29 mg, 60% dispersion in mineral oil, 0.75 mmol), stirred for 20 minutes, treated dropwise with methyl iodide (94 μL, 1.5 mmol), warmed to room temperature, stirred for 18 hours, treated with water, and extracted with ethyl acetate. The extract was concentrated, and the concentrate was used in the next step without further purification.

EXAMPLE 52B 3-amino-4-methoxy-N-methyl-N-(3,4,5-trimethoxyphenyl)benzenesulfonamide A solution of Example 52A (00 mg) in methanol:THF (1 mL: 1 mL) was treated with 10% palladium on carbon, stirred under hydrogen (1 atm) for 4 hours, filtered through diatomaceous earth (Celite®), and concentrated. The concentrate was purified by flash column chromatography on silica gel with 2% methanol/dichloromethane to provide 31 mg of the desired product.

EXAMPLE 52C 3-amino-4-methoxy-N-methyl-N-(3,4,5-trimethoxyphenyl)benzenesulfonamide A solution of Example 52B in less than 1 mL of methanol was treated with several drops of 1M HCl in diethyl ether to provide a cloudy, acidic solution and treated with diethyl ether to precipitate the product. The precipitate was filtered and oven dried to provide 13.5 mg of the desired product.

MS (DCl/NH$_3$) m/z 383 (M+H)$^+$;
$^1$H NMR (300 MHz, DMSO-d$_6$) δ6.83 (d, J=2.1 Hz, 1H), 6.75 (d, J=8.1 Hz, 1H), 6.66 (dd, J=8.1 Hz, 2.1 Hz, 1H), 6.31 (s, 2H), 3.66 (s, 6H), 3.64 (s, 3H), 3.02 (s, 3H).

EXAMPLE 53

1-ethyl-N-(3,4,5-trimethoxyphenyl)-1H-indole-5-sulfonamide

Example 18 (50 mg) was processed as described in Example 19 (substituting ethyl iodide for methyl iodide) to provide 40 mg of the desired product.

MS (DCI/NH$_3$) m/z 391 (M+H)$^+$ and 408 (M+NH$_4$)$^+$;

$^1$H NMR (300 MHz, DMSO-d$_6$) δ9.93 (s, 1H), 8.06 (d, J=2.1 Hz, 1H), 7.70 (d, J=3 Hz, 1H), 7.63 (m, 1H), 7.60 (d, J=2.1 Hz, 1H), 6.62 (d, J=3Hz, 1H), 6.39 (s, 2H), 4.23 (q, J=7.5 Hz, 2H), 3.61 (s, 6H), 3.52 (s, 3H), 1.34 (t, J=7.5 Hz, 3H).

EXAMPLE 54

N-acetyl-3,4,5-trimethoxy-N-(1-methyl-1H-indol-5-yl)benzenesulfonamide

A solution of Example 23 (50 mg, 0.13 mmol) in THF (1 mL) at −25° C. was treated with sequentially with triethylamine (24 μL, 0.17 mmol), lithium chloride (6 mg, 0.14 mmol), and acetic anhydride (25 μL, 0.26 mmol)dropwise, warmed to room temperature, stirred for 18 hours, and concentrated. The concentrate was treated with ethyl acetate and washed with water and brine. The organic layer was dried (Na$_2$SO$_4$), filtered and concentrated. The concentrate was purified by flash column chromatography on silica gel with 1% methanol:dichloromethane to provide 35 mg of the desired product.

MS (DCI/NH$_3$) m/z 419 (M+H)$^+$;

$^1$H NMR (300 MHz, DMSO-d$_6$) δ7.59 (d, J=2.1 Hz, 1H), 7.57 (d, J=8.7 Hz, 1H), 7.47 (d, J=3.3 Hz, 1H), 7.17 (s, 2H), 7.13 (dd, J=8.7, 2.1 Hz, 1H), 6.53 (dd, J=2.1, 3.3 Hz, 1H), 3.86 (s, 6H), 3.85 (s, 3H), 3.73 (s, 3H), 1.81 (s, 3H).

EXAMPLE 55

3,4,5-trimethoxy-N-(6-quinolinyl)benzenesulfonamide

Example 21A (185 mg) was processed as described in Example 21B (substituting 6-aminoquinoline for 4-methoxyaniline) to provide 180 mg of the desired product.

MS (DCI/NH$_3$) m/z 375 (M+H)$^+$;

$^1$H NMR (300 MHz, DMSO-d$_6$) δ10.58 (s, 1H), 8.77 (dd, J=1.5 Hz, 4.0 Hz, 1H), 8.31 (d, J=8.7 Hz 1H), 7.91 (d, J=9 Hz, 1H), 7.68 (d, J=2.4 Hz, 1H), 7.53 (dd, J=9 Hz, 2.4 Hz, 1H), 7.46 (dd, J=8.7 Hz, 4.2 Hz, 1H), 3.73 (s, 6H), 3.65 (s, 3H).

EXAMPLE 56

N-(2-hydroxyethyl)-1-methyl-N-(3,4,5-trimethoxyphenyl)-1H-indole-5-sulfonamide Example 19 (50 mg) was processed as described in Example 38 (substituting ethylene glycol for N,N-dimethyl-2-aminoethanol) to provide 25.5 mg of the desired product.

MS (DCI/NH$_3$) m/z 421 (M+H)$^+$;

$^1$H NMR (300 MHz, DMSO-d$_6$) δ7.86 (d, J=1.8 Hz, 1H), 7.64 (d, J=8.7 Hz, 1H), 7.54 (d, J=3.3 Hz, 1H), 7.32 (dd, J=8.7 Hz, 1.8 Hz, 1H), 6.65 (d, J=3.3 Hz, 1H), 6.29 (s, 2H), 4.03 (q, J=6.9 Hz, 2H), 3.84 (s, 3H), 3.64 (s, 3H), 3.58 (s, 6H), 2.52 (d, J=6.9 Hz, 2H).

EXAMPLE 57

N-(2-fluoroethyl)-1-methyl-N-(3,4,5-trimethoxyphenyl)-1H-indole-5-sulfonamide Example 19 (50 mg) was processed as described in Example 38 (substituting 2-fluoroethanol for N,N-dimethyl-2-aminoethanol) to provide 30 mg of the desired product.

MS (DCI/NH$_3$) m/z 423 (M+H)$^+$;

$^1$H NMR (300 MHz, DMSO-d$_6$) δ7.90 (d, J=1.8 Hz, 1H), 7.64 (d, J=8.7 Hz, 1H), 7.54 (d, J=3.3 Hz, 1H), 7.40 (dd, J=8.7 Hz, 1.8 Hz, 1H), 6.63 (d, J=3.3 Hz, 1H), 6.23 (s, 2H), 4.48 (t, 2H), 4.32 (t, 2H), 3.86 (s, 3H), 3.65 (s, 3H), 3.54 (s, 6H).

EXAMPLE 58

N-ethyl-1-methyl-N-(3,4,5-trimethoxyphenyl)-1H-indole-5-sulfonamide

Example 19 (50 mg) was processed as described in Example 38 (substituting ethanol for N,N-dimethyl-2-aminoethanol) to provide 35 mg of the desired product.

MS (DCI/NH$_3$) m/z 405 (M+H)$^+$;

$^1$H NMR (300 MHz, DMSO-d$_6$) δ7.89 (d, J=1.8 Hz, 1H), 7.64 (d, J=8.7 Hz, 1H), 7.54 (d, J=3.3 Hz, 1H), 7.40 (dd, J=8.7 Hz, 1.8 Hz, 1H), 6.64 (d, J=3.3 Hz, 1H), 6.22 (s, 2H), 3.86 (s, 3H), 3.65 (s, 3H), 3.56 (s, 6H), 3.49 (q, 2H), 0.97 (t, 3H).

EXAMPLE 59

4-nitrophenyl-3,4,5-trimethoxybenzenesulfonate

A solution of 21A (2.02 g, 7.57 mmol) in dichloromethane (31 mL) was treated with 4-nitrophenol (1.06 g, 7.62 mmol), pyridine, and DMAP, stirred overnight at room temperature, diluted with ethyl acetate and washed with 1M Na$_2$CO$_3$. The organic layer was dried (MgSO$_4$), filtered, and concentrated to provide 1.76 g of the title compound.

MS (APCI) m/z 368 (M+H)$^+$;

$^1$H NMR (300 MHz, CDCl$_3$) 8.23 (m, 2H), 7.23 (m, 2H), 7.05 (s, 2H), 3.94 (s, 3H), 3.86 (s, 6H).

EXAMPLE 60

4-aminophenyl-3,4,5-trimethoxybenzenesulfonate

A slurry of Example 59 (917 mg, 2.48 mmol) and Pd/C in ethyl acetate was stirred under hydrogen for 18 hours, filtered and concentrated to provide 741 mg of the desired product.

MS (ESI) m/z 357 (M+NH$_4$)$^+$;

$^1$H NMR (300 MHz, CDCl$_3$) 7.01 (s, 2H), 6.80 (d, J=8.1, 2H), 6.61 (d, J=8.5, 2H), 3.93 (s, 3H), 3.85 (s, 6H).

EXAMPLE 61

4-dimethylaminophenyl-3,4,5-trimethoxybenzenesulfonate

A stirred solution of Example 60 (142 mg, 0.418 mmol) in acetic acid (4.5 mL) was treated with paraformaldehyde (126 mg, 419 mmol) and NaCNBH$_3$ (131 mg, 2.09 mmol), stirred overnight at room temperature, and concentrated. The concentrate was dissolved in ethyl acetate, washed with saturated sodium bicarbonate, dried (MgSO$_4$), filtered, and concentrated to provide 76 mg of the desired product.

MS (ESI) m/z 368 (M+H)$^+$;

$^1$H NMR (300 MHz, CDCl$_3$) 7.01 (s, 2H), 6.84 (d, J=8.8, 2H), 6.57 (d, J=8.8, 2H), 3.92 (s, 3H), 3.83 (s, 6H).

EXAMPLE 62

3,4,5-trimethoxyphenyl 6-methoxy-3-pyridinesulfonate

EXAMPLE 62A

2-methoxy-5-pyridinesulfonylchloride

The procedure in *J. Het. Chem.* 23, 1253 (1986) was slightly modified to make the title compound. A stirred solution of 2-methoxy-5-aminopyridine (1.06 g, 8.61 mmol) in acetic acid (8.2 mL) and 12M HCl (15 mL) at −10° C. was slowly treated with a solution of NaNO$_2$ (633 mg, 9.17 mmol) in water (2.2 mL), stirred at −5° C. for 30 minutes, treated sequentially with a solution of CuCl$_2$ (463 mg, 3.44 mmol), SO$_2$ (4 mL) in acetic acid (11 mL), and water (2 mL), stirred for 2 hours at −5° C. and at room temperature for 18 hours, poured over ice, filtered, and concentrated to provide 725 mg of the desired product.

$^1$H NMR (300 MHz, CDCl$_3$) 8.84 (d, J=2.7, 1H), 8.11 (dd, J=2.7, 8.8, 1H), 6.91 (d, J=9.2, 1H), 4.07 (s, 3H).

EXAMPLE 62B

3,4,5-trimethoxyphenyl 6-methoxy-3-pyridinesulfonate

A solution of 2-methoxypyridine-5-sulfonylchloride (314 mg, 1.51 mmol) in dichloromethane (15 mL) was treated with triethylamine (0.63 mL) and 3,4,5-trimethoxyphenol (279 mg, 1.51 mmol), stirred for 18 hours at room temperature, diluted with ethyl acetate, washed three times with 1M Na$_2$CO$_3$, dried (MgSO$_4$), filtered, and concentrated to provide 447 mg of the desired product.

MS (ESI) m/z 356 (M+H)$^+$;

$^1$H NMR (300 MHz, CDCl$_3$) 8.61 (d, J=2.7, 1H), 7.96 (dd, J=2.4, 11.2, 1H), 6.85 (dd, J=0.7, 9.5, 1H), 6.26 (s, 2H), 4.02 (s, 3H), 3.80 (s, 3H), 3.75 (s, 6H).

EXAMPLE 63

1-methyl-2-oxo-1,2-dihydro-4-pyridinyl 3,4,5-trimethoxybenzenesulfonate

A solution of 4-hydroxy-1-methyl-1H-pyridin-2-one ([40357-87-7], 44.9 mg, 0.358 mmol) in dioxane (2 mL) and DMF (1 mL) was treated with triethylamine (0.15 mL) and 3,4,5-trimethoxybenzenesulfonylchloride (97.1 mg, 0.358 mmol), stirred for 48 hours at room temperature, diluted with ethyl acetate, washed with 1.1M NaHSO$_4$, dried (MgSO$_4$), filtered and concentrated. Chromatography of the concentrate on silica gel with 40% ethyl acetate/hexane provided 47 mg of the desired compound.

MS (ESI) m/z 356 (M+H)$^+$;

$^1$H NMR (300 MHz, CDCl$_3$) 7.29 (d, J=7.5, 1H), 7.11 (s, 2H), 6.21 (d, J=2.4, 1H), 6.13 (dd, J=2.7, 7.5, 1H), 3.94 (s, 3H), 3.92 (s, 6H), 3.51 (s, 3H).

EXAMPLE 64

3,4,5-trimethoxyphenyl 3-((3-aminopropanoyl)amino)-4-methoxybenzenesulfonate A solution of Example 43 (0.148 g, 0.400 mmol) and N-tert-Boc-α-alanine (0.228 g, 1.20 mmol) in DMF (4 mL) was treated with HOOBT (0.260 g, 1.60 mmol), 1-ethyl-3-(3-dimethylaminopropyl)carbodiimide (EDCI) (0.306 g, 1.60 mmol), and triethylamine (0.162 g, 1.60 mmol), heated at 50° C. for 30 hours, cooled, diluted with ethyl acetate (40 mL), washed sequentially with 2:1:1 water/saturated aqueous sodium bicarbonate/brine (20 mL followed by 2×10 mL) and brine (10 mL), filtered through silica gel with ethyl acetate rinses, and concentrated. The concentrate was purified by radial chromatography with 1:1 hexane/ethyl acetate to provide 0.138 g of the N-Boc amide. The amide was stirred in 4M HCl in dioxane (2 mL) for two hours and concentrated. The concentrate was dissolved in a minimal amount of water and lyophilized to provide 0.123 g of the desired product.

LRMS (ESI(+)) m/z 441 (M+H)$^+$; (ES[(−)) m/z 439 (M−H)$^−$;

$^1$H NMR (DMSO-d$_6$) δ2.82 (t, J=6.4 Hz, 3H), 3.06 (t, J=6.4 Hz, 3H), 3.61 (s, 3H), 3.63 (s, 6H), 3.96 (s, 3H), 6.30 (s, 2H), 7.29 (d, J=8.8 Hz, 1H), 7.60 (dd, J=2.2, 8.8 Hz, 1H), 7.75–7.81 (br, 3H), 8.62 (d, J=2.2 Hz, 1H), 9.85–9.89 (br, 1H).

EXAMPLE 65

3,4,5-trimethoxyphenyl 3-(((2R)-2-aminopropanoyl)amino)-4-methoxybenzenesulfonate Example 43 was processed as described in Example 64 but substituting N-t-Boc-alanine for N-tert-Boc-β-alanine to provide the desired product.

LRMS (ESI(+)) m/z 441 (M+H)$^+$; (ESI(−)) m/z 439 (M−H)$^−$;

$^1$H NMR (DMSO-d$_6$) δ1.44 (d, J=6.7 Hz, 3H), 3.61 (s, 3H), 3.63 (s, 6H), 3.98 (s, 3H), 4.19–4.28 (br, 1H), 6.31 (s, 2H), 7.43 (d, J=8.9 Hz, 1H), 7.67 (dd, J=2.4, 8.9 Hz, 1H), 8.25–8.32 (br, 3H), 8.49 (d, J=2.4 Hz, 1H), 10.17 (s, 1H).

EXAMPLE 66

3,4,5-trimethoxyphenyl 3-(((2R)-2-amino-3-methylbutanoyl)amino)-4-methoxybenzenesulfonate Example 43 was processed as described in Example 64 but substituting N-t-Boc-valine for N-tert-Boc-β-alanine to provide the desired product.

LRMS (ESI(+)) m/z 469 (M+H)$^+$; (ESI(−)) m/z 467 (M−H)$^−$;

$^1$H NMR (DMSO-d$_6$) δ0.98 (d, J=7.0 Hz, 6H), 2.09–2.21 (m, 1H), 3.61 (s, 3H), 3.63 (s, 6H), 3.98 (s, 3H), 4.04 (d, J=5.2 Hz, 1H), 6.30 (s, 2H), 7.35 (d, J=9.0 Hz, 1H), 7.69 (dd, J=2.2, 9.0 Hz, 1H), 8.18–8.34 (Br, 3H), 8.46 (d, J=2.2 Hz, 1H), 10.17–10.21 (Br, 1 H).

EXAMPLE 67

N-((dimethylamino)acetyl)-1-methyl-N-(3,4,5-trimethoxyphenyl)-1H-indole-5-sulfonamide A solution of Example 19 (1.00 g, 2.66 mmol) in dichloromethane (25 mL) at room temperature was treated with DCC (2.75 g, 13.3 mmol), 4-pyrrolidinylpyridine (0.20 g, 1.32 mmol) and N,N-dimethylglycine (0.68 g, 6.40 mmol), stirred for 16 hours, diluted with dichloromethane, and filtered. The filtrate was washed with water, dried (MgSO$_4$), filtered, and concentrated. The concentrate was treated with dichloromethane, filtered, and concentrated. The concentrate was purified by flash column chromatography on silica gel with 1.5% methanol/dichloromethane, dissolved in dichloromethane (5 mL) and diethyl ether (5 mL), treated with 4M HCl in dioxane (0.55 mL), stirred for 10 minutes, treated with ether, and filtered to provide the desired product.

mp: 200–203° C.;

MS (ESI(+)) m/z 462 (M+H)$^+$;

$^1$H NMR (DMSO-d$_6$): δ8.36 (d, J=1.8 Hz, 1H), 7.78 (dd, J$_1$=8.7 Hz, J$_2$=1,8 Hz, 1H), 7.73 (d, J=8.7 Hz, 1H), 7.61 (d, J=3.0 Hz, 1H), 6.76 (d, J=3.0 Hz, 1H), 6.73 (s, 2H), 3.92 (s, 2H), 3.82 (s, 3H), 3.82 (s, 6H), 3.75 (s, 3H), 2.67 (s, 6H);

Anal. calcd. for C$_{22}$H$_{27}$N$_3$O$_6$S.HCl1.5H$_2$O: C, 50.43; H, 5.77; N, 8.02. Found: C, 50.50; H, 5.93; N, 8.01.

EXAMPLE 68

1-methyl-N-(((2S)-1-methylpyrrolidinyl)carbonyl)-N-(3,4,5-trimethoxyphenyl)-1H-indole-5-sulfonamide The desired product was prepared by substituting N-methyl-L-proline for N,N-dimethylglycine in Example 67.

MS (APCI(+)) m/z 488 (M+H)+;
¹H NMR (DMSO-d₆) δ8.36 (d, J=2 Hz, 1H), 7.75 (m, 2H), 7.61 (d, J=3 Hz, 1H), 6.82 (s, 2H), 4.76 (d, J=3 Hz, 1H), 4.06 (m, 1H), 3.90 (s, 3H), 3.81 (s, 6H), 3.77 (s, 3H), 3.00 (m, 2H), 2.69 (s, 3H), 1.90 (m, 3H), 1.73 (m, 1H).

EXAMPLE 69

N-((2S)-2-(dimethylamino)-3-methylbutanoyl)-1-methyl-N-(3,4,5-trimethoxyphenyl)-1H-indole-5-sulfonamide The desired product was prepared by substituting N,N-dimethyl-L-valine for N,N-dimethylglycine in Example 67.

MS (ESI(+)) m/z 504 (M+H)+;
¹H NMR (DMSO-d₆) δ8.38 (s, 1H), 7.75 (m, 2H), 7.60 (d, J=3Hz, 1H), 6.76 (d, J=3 Hz, 1H), 6.55 (br s, 2H), 3.89 (s, 3H), 3.82 (m, 1H), 3.79 (s, 9H), 2.68 (m, 3H), 2.55 (br s, 3H), 2.26 (br s, 1H), 0.91 (m, 3H), 0.75 (m, 3H).

EXAMPLE 70

N-((2S)-2-amino-3-methyl butanoyl)-1-methyl-N-(3,4,5-trimethoxyphenyl)-1H-indole-5-sulfonamide A solution of Example 19 (400 mg, 1.06 mmol) in dichloromethane (8 mL) at room temperature was treated with DCC (482 mg, 2.42 mmol), 4-pyrrolidinopyridine (16 mg, 0.11 mmol), and N-(tert-butoxycarbonyl)-L-valine (462 mg, 2.13 mmol), stirred for 16 hours, treated with additional DCC (50 mg, 0.25 mmol) and N-(tert-butoxycarbonyl)-L-valine (50 mg, 0.23 mmol), stirred for 4 hours, and filtered. The filtrate was treated with dichloromethane (50 mL), washed with water, dried (Na₂SO₄), filtered, and concentrated. The concentrate was purified by flash column chromatography on silica gel with 2% methanol/dichloromethane, dissolved in dioxane (5 mL), treated with 4M HCl in dioxane, stirred for 2 hours, treated with ether (75 mL), filtered, and dried to provide the desired product.

MS (ESI(+)) m/z 576 (M+H)+;
¹H NMR (DMSO-d₆) δ8.33 (m, 1H), 7.73 (m, 2H), 7.60 (d, J=3 Hz, 1H), 6.75 (d, J=3 Hz, 1H), 6.65 (br s, 2H), 3.80 (br s, 7H), 3.76 (s, 3H), 3.57 (s, 3H), 2.10 (m, 1H), 0.80 (d, J=2.4 Hz, 3H), 0.78 (d, J=2.7 Hz, 3H).

EXAMPLE 71

1-methyl-N-((2S)-2-(methylamino)propanoyl)-N-(3,4,5-trimethoxyphenyl)-1H-indole-5-sulfonamide The desired product was prepared by substituting N-(tert-butoxycarbonyl)-L-N-methylalanine for N-(tert-butoxycarbonyl)-L-valine in Example 70.

MS (DCI/NH₃) m/z 462 (M+H)+;
¹H NMR (DMSO-d6) δ8.95 (br s, 2H), 8.33 (m, 1H), 7.68–7.78 (m, 2H), 7.60 (d, J=4 Hz, 1H), 6.72 (d, J=4 Hz, 1H), 6.70 (br s, 2H), 3.89 (s, 3H), 3.81 (s, 6H), 3.77 (s, 3H), 3.62–3.71 (m, 1H), 2.37 (s, 3H), 1.38 (d, J=8 Hz, 3H).

EXAMPLE 72

N-((2R)-2-amino-2-phenylethanoyl)-1-methyl-N-(3,4,5-trimethoxyphenyl)-1H-indole-5-sulfonamide The desired product was prepared by substituting (S)-N-(tert-butoxycarbonyl)-2-phenylglycine for N-(tert-butoxycarbonyl)-L-valine in Example 70.

MS (ESI(+)) m/z 510 (M+H)+; 532 (M+Na)+;
¹H NMR (DMSO-d₆) δ8.52 (br s, 3H), 8.34 (m, 1H), 7.74 (s, 1H), 7.63(d, J=3.4 Hz, 1H), 7.41–7.27 (m, 3 H), 6.83–6.67 (m, 4H), 5.51 (br s, 1H), 4.92 (s, 1H), 3.91 (s, 3H), 3.87–3.85 (m, 3H), 3.73 (s, 3H), 3.57 (s, 3H).

EXAMPLE 73

N-((2S)-2-amino-3-phenylpropanoyl)-1-methyl-N-(3,4,5-trimethoxyphenyl)-1H-indole-5-sulfonamide The desired product was prepared by substituting N-(tert-butoxycarbonyl)-L-phenylalanine for N-(tert-butoxycarbonyl)-L-valine in Example 70.

MS (ESI(+)) m/z 524 (M+H)+; 546 (M+Na)+;
¹H NMR (DMSO-d₆) δ8.44 (br s, 3H), 8.32 (m, 1H), 7.74 (d, J=1.6 Hz, 1H), 7.63 (d, J=3.4 Hz, 1H), 7.28–7.11 (m, 3H), 6.82–6.77 (m, 4H), 6.00 (br s, 1H), 3.91 (s, 3H), 3.72–3.67 (m, 9H).

EXAMPLE 74

1-methyl-N-((2S)-pyrrolidinylcarbonyl)-N-(3,4,5-trimethoxyphenyl)-1H-indole-5-sulfonamide The desired product was prepared by substituting N-(tert-butoxycarbonyl)-L-proline for N-(tert-butoxycarbonyl)-L-valine in Example 70.

MS (ESI(+)) m/z 474 (M+H)+;
¹H NMR (DMSO-d₆) δ8.35 (m, 1H), 7.76 (m, 2H), 7.61 (d,+J=3 Hz, 1H), 6.75 (d, J=3 Hz, 1H), 6.70 (br s, 2H), 4.03 (m, 1H), 3.89 (s, 3H), 3.81 (br s, 6H), 3.76 (s, 3H), 3.20 (m, 2H), 1.95–1.75 (m, 4H).

EXAMPLE 75

N-((2S)-2,6-diaminohexanoyl)-1-methyl-N-(3,4,5-trimethoxyphenyl)-1H-indole-5-sulfonamide The desired product was prepared by substituting N,N-di-(tert-butoxycarbonyl)-L-lysine for N-(tert-butoxycarbonyl)-L-valine in Example 70.

MS (ESI(+)) m/z 505 (M+H)+;
¹H NMR (DMSO-d₆) δ8.30 (m, 1H), 7.73 (m, 2H), 7.60 (d, J=3 Hz, 1H), 6.75 (d, J=3 Hz, 1H), 6.65 (br s, 2H), 3.89 (s, 3H), 3.80 (m, 6H), 3.76 (s, 3H), 3.59 (m, 1H), 2.67 (m, 2H), 1.75–1.20 (m, 6H).

EXAMPLE 76

N-((2S)-2-amino-3-(1H-imidazol-5-yl)propanoyl)-1-methyl-N-(3,4,5-trimethoxyphenyl)-1H-indole-5-sulfonamide The desired product was prepared by substituting N-(tert-butoxycarbonyl)-L-histidine for N-(tert-butoxycarbonyl)-L-valine in Example 70.

mp: 175–177° C.;
MS (ESI(+)) m/z 514 (M+H)+;
¹H NMR (DMSO-d₆) δ9.03 (s, 1H), 8.29 (s, 1H), 7.71 (m, 2H), 7.61 (d, J=3 Hz, 1H), 7.28 (s, 1H), 6.75 (d, J=3 Hz, 1H), 6.70 (br s, 2H), 4.01 (m, 1H), 3.89 (s, 3H), 3.79 (br s, 6H), 3.76 (s, 3H), 1.72 (m, 2H).

EXAMPLE 77

(2S)-2-amino-4-oxo-4-(3,4,5-trimethoxy((1-methyl-1H-indol-5-yl)sulfonyl)anilino)butanoic acid The desired product was prepared by substituting N-(tert-butoxycarbonyl)-L-aspartic acid 1-tert-butyl ester for N-(tert-butoxycarbonyl)-L-valine in Example 70.

mp: 156–159° C.;

MS (ESI(+)) m/z 492 (M+H)$^+$;

$^1$H NMR (DMSO-d$_6$) δ8.35 (d, J=2 Hz), 7.75 (m, 2H), 7.60 (d, J=1 H), 6.73 (d, J=3 Hz, 1H), 6.63 (br s, 2H), 4.01 (m, 1H), 3.88 (s, 3H), 3.82 (s, 6H), 3.76 (s, 3H), 2.80–2.70 (m, 2H).

EXAMPLE 78

(3S)-3-amino-4-oxo-4-(3,4,5-trimethoxy((1-methyl-1H-indol-5-yl)sulfonyl)anilino)butanoic acid The desired product was prepared by substituting N-(tert-butoxycarbonyl)-L-aspartic acid 4-tert-butyl ester for N-(tert-butoxycarbonyl)-L-valine in Example 70.

MS (ESI(+)) m/z 492 (M+H)$^+$;

$^1$H NMR (DMSO-d$_6$): δ8.33 (m, 1H), 7.73 (m, 2H), 7.61 (d, J=3 Hz, 1H), 6.62 (d, J=3 Hz, 1H), 6.40 (s, 2H), 3.95 (m, 1H), 3.88 (s, 3H), 3.76 (s, 6H), 3.74 (s, 3H), 2.75 (m, 2H).

EXAMPLE 79

(2R)-2-amino-5-oxo-5-(3,4,5-trimethoxy((1-methyl-1H-indol-5-yl)sulfonyl)anilino)pentanoic acid The desired product was prepared by substituting N-(tert-butoxycarbonyl)-L-glumatic acid 1-tert-butyl ester for N-(tert-butoxycarbonyl)-L-valine in Example 70.

MS (ESI(+)) m/z 506 (M+H)$^+$;

$^1$H NMR (DMSO-d$_6$) δ8.31 (br s, 1H), 7.75 (dd, J$_1$=9 Hz, J$_2$=2 Hz, 1H), 7.69 (d, J=9 Hz, 1H), 7.58 (d, J=3 Hz, 1H), 6.72 (d, J=3 Hz, 1H), 6.69 (s, 1H), 6.66 (s, 1H), 4.06 (m, 1H), 3.88 (s, 3H), 3.80 (s, 6H), 3.72 (s, 3H), 2.30 (m, 1H), 2.22 (m, 1H), 1.95 (m, 1H), 1.80 (m, 1H).

EXAMPLE 80

(4S)-4-amino-5-oxo-5-(3,4,5-trimethoxy((1-methyl-1H-indol-5-yl)sulfonyl)anilino)pentanoic acid The desired product was prepared by substituting N-(tert-butoxycarbonyl)-L-glumatic acid 5-tert-butyl ester for N-(tert-butoxycarbonyl)-L-valine in Example 70.

MS (ESI(+)) m/z 506 (M+H)$^+$;

$^1$H NMR (DMSO-d$_6$) δ8.33 (m, 1H), 7.74 (m, 2H), 7.60 (d, J=3 Hz, 1H), 6.75 (d, J=3 Hz, 1H), 6.71 (br s, 2H), 4.06 (m, 1H), 3.89 (s, 3H), 3.80 (s, 6H), 3.75 (s, 3H), 3.72 (s, 3H), 2.19 (m, 2H), 1.95–1.70 (m, 2H).

EXAMPLE 81

N-((bis(2-methoxyethyl)amino)acetyl)-1-methyl-N-(3,4,5-trimethoxyphenyl)-1H-indole-5-sulfonamide

EXAMPLE 81A benzyl (bis(2-methoxyethyl)amino)acetate

A solution of benzyl bromoacetate (28.9 g; 96.7 mmol) in dichloromethane (100 mL) at room temperature was treated with 2-methoxy-N-(2-methoxyethyl)ethanamine (40.6 g; 305 mmol), stirred for 30 minutes, diluted with dichloromethane, washed sequentially with saturated NH$_4$Cl, water, and brine, dried (Na$_2$SO$_4$), filtered, and concentrated. The concentrate was purified by flash column chromatography on silica gel with 40% diethyl ether/dichloromethane to provide the desired product.

EXAMPLE 81B 5 (bis(2-methoxyethyl)amino)acetic acid

A solution of Example 81A (19.4 g; 69 mmol) and 10% Pd/C (3.5 g) in methanol (150 mL) at room temperature was stirred under 4 atm of H$_2$ for 17 hours, filtered through diatomaceous earth (Celite®), and concentrated to provide the desired product.

EXAMPLE 81C

N-((bis(2-methoxyethyl)amino)acetyl)-1-methyl-N-(3,4,5-trimethoxyphenyl)-1H-indole-5-sulfonamide The desired product was prepared by substituting Example 81B for N,N-dimethylglycine in Example 67.

MS (DCI/NH$_3$) m/z 550 (M+H)$^+$;

$^1$H NMR (DMSO-d$_6$) δ8.29 (d, J=2Hz, 1H), 7.77–7.68 (m, 2H), 7.57 (d, J=4 Hz, 1H), 6.73 (d, J=4 Hz, 1H), 6.61 (s, 2H), 3.88 (s, 3H), 3.78 (s, 6H), 3.72 (s, 3H), 3.19 (s, 2H), 3.16 (t, J=6 Hz, 4H), 3.04 (s, 6H), 2.61 (t, J=6 Hz, 4H);

Anal. calcd. for C$_{26}$H$_{36}$ClN$_3$O$_8$S: C, 53.28; H, 6.19; N, 7.17; Cl, 6.05. Found: C, 53.28; H, 6.03; N, 7.10; Cl, 5.97.

EXAMPLE 82

1-methyl-N-(4-morpholinylacetyl)-N-(3,4,5-trimethoxyphenyl)-1H-indole-5-sulfonamide The desired product was prepared by substituting morpholine for 2-methoxy-N-(2-methoxyethyl)ethanamine in Example 81.

MS (DCI/NH$_3$) m/z 504 (M+H)$^+$;

$^1$H NMR (DMSO-d$_6$) δ8.29–7.77 (d, J=2 Hz, 1H), 7.68 (m, 2H), 7.57 (d, J=4 Hz, 1H), 6.73 (d, J=4 Hz, 1H), 6.63 (s, 2H), 3.88 (s, 3H), 3.80 (s, 6H), 3.72 (s, 3H), 3.47–3.41 (m, 4H), 2.94 (s, 2H), 2.31–2.27 (m, 4H).

EXAMPLE 83

1-methyl-N-((4-methyl-1-piperazinyl)acetyl)-N-(3,4,5-trimethoxyphenyl)-1H-indole-5-sulfonamide The desired product was prepared by substituting N-methylpiperazine for 2-methoxy-N-(2-methoxyethyl)ethanamine in Example 81.

MS (DCI/NH$_3$) m/z 517 (M+H)$^+$;

$^1$H NMR (DMSO-d$_6$) δ8.29 (d, J=2 Hz, 1H), 7.77–7.68 (m, 2H), 7.57 (d, J=4 Hz, 1H), 6.73 (d, J=4 Hz, 1H), 6.61 (s, 2H), 3.88 (s, 3H), 3.78 (s, 6H), 3.72 (s, 3H), 2.91 (s, 2H), 2.29–2.13 (m, 8H), 2.07 (s, 3H).

EXAMPLE 84

N-(4-(aminomethyl)benzoyl)-1-methyl-N-(3,4,5-trimethoxyphenyl)-1H-indole-5-sulfonamide

EXAMPLE 84A 4-(((tert-butoxycarbonyl)amino)methyl)benzoic acid

A solution of 4-(aminomethyl)benzoic acid (1.51 g, 10 mmol), di(tert-butyl) dicarbonate (2.62 g, 12 mmol), and sodium hydroxide (0.48 g, 12 mmol) in tert-butanol (20 mL) was stirred for 16 hours, treated with water (200 mL), and extracted with hexanes. The aqueous layer was cooled to 5° C., adjusted to pH 4 with 1M NaHSO$_4$, and extracted with ethyl acetate. The combined extracts were dried (Na$_2$SO$_4$), filtered, and concentrated to provide the desired product.

MS (ESI(+)) m/z 252 (M+H)$^+$, 269 (M+NH$_4$)$^+$;

$^1$H NMR (DMSO-d$_6$) δ8.06 (d, J=8.5 Hz, 2H), 7.38 (d, J=8.5 Hz, 2H), 4.95 (br s, 1H), 4.40 (d, J=5.9 Hz, 2 H), 1.48 (s, 9H).

EXAMPLE 84B

N-(4-(aminomethyl)benzoyl)-1-methyl-N-(3,4,5-trimethoxyphenyl)-1H-indole-5-sulfonamide The desired product was prepared by substituting Example 84A for N-(tert-butoxycarbonyl)-L-valine in Example 70.

MS (ESI(+)) m/z 510 (M+H)$^+$;

$^1$H NMR (DMSO-d$_6$) δ8.35 (br s, 3H), 8.24 (m, 1H), 7.74 (s, 1H), 7.68(m, 2H), 7.59 (m, 3 H), 7.34 (m, 2H), 6.73 (m, 1H), 6.57 (s, 2H), 3.95 (m, 2H), 3.88 (s, 3H), 3.64 (m, 6H), 3.56 (s, 3H).

EXAMPLE 85

1,2,3-trimethoxy-5-((4-methoxybenzyl)sulfanyl)benzene

EXAMPLE 85A 3,4,5-trimethoxybenzenethiol

A room temperature suspension of zinc powder (430 mg, 6.56 mmol) and dichlorodimethylsilane (0.80 mL, 6.59 mmol) in 1,2-dichloroethane (15 mL) was treated with a solution of 3,4,5-trimethoxybenzenesulfonyl chloride (500 mg, 1.87 mmol) and 1,3-dimethyl-2-imidazolidinone (647 mg, 5.67 mmol) in 1,2-dichloroethane (15 mL). The reaction was heated to 75° C. for 1 hour, cooled to room temperature, filtered, and concentrated. The concentrate was dissolved in methanol, concentrated, dissolved in methanol, and concentrated. The concentrate was purified by flash column chromatography on silica gel with dichloromethane to provide the desired product.

EXAMPLE 85B 1,2,3-trimethoxy-5-((4-methoxybenzyl)sulfanyl)benzene

A room temperature solution of Example 85A (194 mg, 0.97 mmol), 1-(chloromethyl)-4-methoxybenzene (162 mg, 1.03 mmol), and KOH (70 mg, 1.25 mmol) in DMF (5 mL) was stirred for 2 hours, treated with saturated NH$_4$Cl, and extracted with ethyl acetate. The combined extracts were washed with brine, dried (MgSO$_4$), filtered, and concentrated. The concentrate was purified by flash column chromatography on silica gel with 25% ethyl acetate/hexanes to provide the desired product.

mp 65–67° C.;

MS (DCI/NH$_3$) m/e 321 (M+H)$^+$;

$^1$H NMR (300 MHz, DMSO-d$_6$) δ7.27 (d, J=9 Hz, 2H), 6.87 (d, J=9 Hz, 2H), 6.59 (s, 2H), 4.19 (s, 2H), 3.72 (s, 3H), 3.61 (s, 3H), 3.32 (s, 6H);

Anal. calcd. for C$_{17}$H$_{20}$O$_4$S: C, 63.72; H, 6.29. Found: C, 63.71; H, 6.39.

EXAMPLE 86

1,2,3-trimethoxy-5-((4-methoxybenzyl)sulfinyl)benzene

A room temperature mixture of Example 85B (100 mg, 0.31 mmol), acetic anhydride (38 mg, 0.37 mmol), and silica gel (65 mg) in dichloromethane (1.5 mL) was treated with 30% H$_2$O$_2$ (45 mL), stirred for 16 hours, filtered, and washed with dichloromethane. The filtrate was washed sequentially with 10% Na$_2$SO$_3$, saturated NaHCO$_3$, and brine, dried (Na$_2$SO$_4$), filtered, and concentrated. The concentrate was purified by flash column chromatography on silica gel with 1% methanol/dichloromethane to provide the desired product.

mp 103–105° C.;

MS (DCI/NH$_3$) m/e 337 (M+H)$^+$;

$^1$H NMR (300 MHz, DMSO-d$_6$) δ7.01 (d, J=9 Hz, 2H), 6.87 (d, J=9 Hz, 2H), 6.74 (s, 2H), 4.08 (dd, J=8 Hz, 54 Hz, 2H), 3.72 (s, 3H), 3.68 (s, 3H), 3.32 (s, 6H);

Anal. calcd. for C$_{17}$H$_{20}$O$_5$S: C, 60.70; H, 5.99. Found: C, 60.77; H, 5.82.

EXAMPLE 87

1,2,3-trimethoxy-5-((4-methoxybenzyl)sulfonyl)benzene

A solution of Example 85B (160 mg, 0.50 mmol) in acetone (3 mL) was treated with water (3 mL), NaHCO$_3$ (500 mg), and potassium peroxymonosulfate (OXONE®) (415 mg, 0.67 mmol), stirred for 3 hours, diluted with water, treated with solid Na$_2$SO$_3$, and extracted with ethyl acetate. The combined extracts were washed with water and brine, dried (MgSO$_4$), filtered, and concentrated to provide the desired product.

mp 95–97° C.;

MS (DCI/NH$_3$) m/e 370 (M+NH$_4$)$^+$;

$^1$H NMR (300 MHz, DMSO-d$_6$) δ7.09 (d, J=9 Hz, 2H), 6.91 (s, 2H), 6.87 (d, J=9 Hz, 2H), 4.58 (s, 2H), 3.77 (s, 3H), 3.72 (s, 3H), 3.32 (s, 6H);

Anal. calcd. for C$_{17}$H$_{20}$O$_6$S: C, 57.94; H, 5.72. Found: C, 57.95; H, 5.68.

EXAMPLE 88

1,2,3-tri methoxy-5-((1-(4-methoxyphenyl)-1-methylethyl)sulfonyly)benzene

A 0° C. solution of Example 87 (105 mg, 0.30 mmol) in THF (2 mL) was treated with 1.0M lithium hexamethyldisilazide in THF (0.36 mL, 0.36 mmol), stirred for 15 minutes, treated with iodomethane (80 mg, 0.56 mmol), stirred for 15 minutes, treated with a second portion of 1.0 M lithium hexamethyldisilazide in THF (0.36 mL, 0.36 mmol), stirred for 15 minutes, treated with iodomethane (80 mg, 0.56 mmol), stirred for 15 minutes, acidified with 10% HCl, and extracted with ethyl acetate. The combined extracts were washed with brine, dried (MgSO$_4$), filtered, and concentrated. The concentrate was purified by flash column chromatography on silica gel with 30% ethyl acetate/hexanes to provide the desired product.

MS (DCI/NH$_3$) m/e 398 (M+NH$_4$)$^+$;

$^1$H NMR (300 MHz, DMSO-d$_6$) δ7.27 (d, J=9 Hz, 2H), 6.87 (d, J=9 Hz, 2H), 6.48 (s, 2H), 3.75 (s, 3H), 3.72 (s, 3H), 3.63 (s, 6H), 1.70 (s, 6H);

Anal. calcd. for C$_{19}$H$_{24}$O$_6$S: C, 59.98; H, 6.36. Found: C, 59.71; H, 6.38.

EXAMPLE 89

2-methoxy-5-(((3,4,5-trimethoxyphenyl)sulfanyl)methyl)aniline

EXAMPLE 89A 1,2,3-trimethoxy-5-((4-methoxy-3-nitrobenzyl)sulfanyl)benzene

The desired product was prepared by substituting 4-(chloromethyl)-2-nitrophenyl methyl ether for 1-(chloromethyl)4-methoxybenzene in Example 95.

EXAMPLE 89B 2-methoxy-5-(((3,4,5-trimethoxyphenyl)sulfanyl)methyl)aniline

A room temperature suspension of zinc dust (2.35 g) in acetic acid (20 mL) was treated dropwise with a solution of Example 89A (100 mg, 0.27 mmol) and acetic acid (0.40 mL) in dichloromethane (1 mL), stirred at room temperature for 30 minutes, diluted with ethyl acetate (100 mL), filtered, and concentrated. The concentrate was dissolved in ethyl acetate, washed with saturated $NaHCO_3$ and brine, dried ($MgSO_4$), filtered, and concentrated. The concentrate was purified by flash column chromatography on silica gel with 5% ethyl acetate/dichloromethane to provide the desired product.

MS ($DCI/NH_3$) m/e 336 $(M+H)^+$;

$^1$H NMR (300 MHz, DMSO-$d_6$) δ6.70–6.65 (m, 2H), 6.58 (s, 2H), 6.50 (m, 1H), 4.68 (s, 2H), 4.05 (s, 2H), 3.72 (s, 6H), 3.71 (s, 3H), 3.63 (s, 3H).

EXAMPLE 90

2-methoxy-5-(((3,4,5-trimethoxyphenyl)sulfinyl)methyl)aniline

EXAMPLE 90A 1,2,3-trimethoxy-5-((4-methoxy-3-nitrobenzyl)sulfinyl)benzene

The desired product was prepared by substituting Example 99A for Example 95B in Example 96.

EXAMPLE 90B 2-methoxy-5-(((3,4,5-trimethoxyphenyl)sulfinyl)methyl)aniline

A room temperature solution of Example 90A (75 mg, 0.20 mmol) in ethanol (5 mL) was treated with 10% Pd/C (10 mg), stirred under a hydrogen atmosphere for 3 hours, heated to reflux, stirred for 3 hours, cooled to room temperature, filtered through diatomaceous earth (Celite®), and concentrated. The concentrate was purified by flash column chromatography with 50% ethyl acetate/dichloromethane to provide the desired product.

MS ($DCI/NH_3$) m/e 352 $(M+H)^+$;

$^1$H NMR (300 MHz, DMSO-$d_6$) δ6.80 (s, 2H), 6.71 (d, J=8 Hz, 1H), 6.50 (d, J=3 Hz, 1H), 6.31 (dd, J=3 Hz, 8 Hz, 1H), 4.76 (s, 2H), 3.93 (dd, J=15 Hz, 45 Hz, 2H), 3.79 (s, 6H), 3.73 (s, 3H), 3.70 (s, 3H);

Anal. calcd. for $C_{17}H_{21}NO_5S$: C, 58.10; H, 6.02; N, 3.99. Found: C, 58.14; H, 5.92; N, 3.85.

EXAMPLE 91

2-methoxy-5-(((3,4,5-trimethoxyphenyl)sulfonyl)methyl)aniline

EXAMPLE 91A 1,2,3-trimethoxy-5-((4-methoxy-3-nitrobenzyl)sulfonyl)benzene

The desired product was prepared by substituting Example 89A for Example 85B in Example 87.

EXAMPLE 91B 2-methoxy-5-(((3,4,5-trimethoxyphenyl)sulfonyl)methyl)aniline

A solution of Example 91A (490 mg, 1.23 mmol) in methanol (10 mL) was treated with $SnCl_2 \cdot 2H_2O$ (1.39 g; 6.17 mmol), heated to reflux for 1 hour, and concentrated. The concentrate was partitioned between saturated $NaHCO_3$ and ethyl acetate, and the aqueous phase was extracted with ethyl acetate. The combined extracts were dried ($MgSO_4$), filtered, and concentrated. The concentrate was purified by flash column chromatography on silica gel with 10% ethyl acetate/dichloromethane to provide the desired product.

MS ($DCI/NH_3$) m/e 385 $(M+NH_4)^+$;

$^1$H NMR (300 MHz, DMSO-$d_6$) δ6.92 (s, 2H), 6.70 (d, J=8 Hz, 1H), 6.53 (d, J=3 Hz, 1H), 6.30 (dd, J=3 Hz, 8 Hz, 1H), 4.76 (s, 2H), 4.44 (s, 2H), 3.79 (s, 6H), 3.73 (s, 6H).

EXAMPLE 92

2-methoxy-5-(1-methyl-1-((3,4,5-trimethoxyphenyl)sulfonyl)ethyl)aniline

EXAMPLE 92A 1,2,3-trimethoxy-5-((1-(4-methoxy-3-nitrophenyl)-1-methylethyl)sulfonyl)benzene The desired product was prepared by substituting Example 91A for Example 87 in Example 88.

EXAMPLE 92B 2-methoxy-5-(1-methyl-1-((3,4,5-trimethoxyphenyl)sulfonyl)ethyl)aniline The desired product was prepared by substituting Example 92A for Example 90A in Example 90B.

MS ($DCI/NH_3$) m/e 413 $(M+NH_4)^+$;

$^1$H NMR (300 MHz, DMSO-$d_6$) δ6.72 (d, J=3 Hz, 1H), 6.69 (d, J=8 Hz, 1H), 6.50 (s, 2H), 6.44 (dd, J=3 Hz, 9 Hz, 1H), 4.71 (s, 2H), 3.76 (s, 3H), 3.72 (s, 3H), 3.64 (s, 6H), 1.63 (s, 6H);

Anal. calcd. for $C_{19}H_{25}NO_6S$: C, 57.70; H, 6.37; N, 3.54. Found: C, 57.56; H. 6.27; N, 3.60.

EXAMPLE 93

1,2,3-trimethoxy-5-(((4-methoxyphenyl)sulfanyl)methyl)benzene

The desired product was prepared by substituting 4-methoxybenzenethiol and 5-(chloromethyl)-1,2,3-trimethoxybenzene for Example 85A and 1-(chloromethyl)-4-methoxybenzene, respectively, in Example 85B.

MS ($DCI/NH_3$) m/e 321 $(M+H)^+$;

$^1$H NMR (300 MHz, DMSO-$d_6$) δ7.30 (d, J=8 Hz, 2H), 6.89 (d, J=8 Hz, 2H), 6.51 (s, 2H), 4.02 (s, 2H), 3.73 (s, 3H), 3.68 (s, 6H), 3.33 (s, 3H).

EXAMPLE 94

1,2,3-trimethoxy-5-(((4-methoxyphenyl)sulfonyl)methyl)benzene

The desired product was prepared by substituting Example 93 for Example 85B in Example 87.

MS ($DCI/NH_3$) m/e 370 $(M+NH_4)^+$;

$^1$H NMR (300 MHz, DMSO-$d_6$) δ7.62 (d, J=8 Hz, 2H), 7.11 (d, J=8 Hz, 2H), 6.38 (s, 2H), 4.51 (s, 2H), 3.85 (s, 3H), 3.63 (s, 3H), 3.61 (s, 6H).

EXAMPLE 95

1,2,3-trimethoxy-5-(1-((4-methoxyphenyl)sulfonyl)-1-methylethyl)benzene

The desired product was prepared by substituting Example 94 for Example 87 in Example 88.

MS (DCI/NH$_3$) m/e 398 (M+NH$_4$)$^+$;
$^1$H NMR (300 MHz, DMSO-d$_6$) δ7.31 (d, J=8 Hz, 2H), 7.03 (d, J=8 Hz, 2H), 6.51 (s, 2H), 3.82 (s, 3H), 3.67 (s, 3H), 3.65 (s, 6H), 1.69 (s, 6H).

EXAMPLE 96

2-methoxy-5-((3,4,5-trimethoxybenzyl)sulfonyl) aniline

EXAMPLE 96A sodium 4-methoxy-3-nitrobenzenesulfinate

A solution of Na$_2$SO$_3$ (400 mg, 3.2 mmol) and NaHCO$_3$ (270 mg, 3.2 mmol) in H$_2$O (10 mL) was treated slowly with a solution of 4-methoxy-3-nitrobenzenesulfonyl chloride (400 mg, 1.6 mmol) in acetone (3 mL), heated to 50° C. for 2 hours, cooled to room temperature, and washed with dichloromethane. The aqueous wash was filtered through cotton, lyophilized, suspended in methanol, filtered, concentrated, and dried under vacuum to provide the desired product.

EXAMPLE 96B 1,2,3-trimethoxy-5-(((4-methoxy-3-nitrophenyl) sulfonyl)methyl)benzene A suspension of Example 96A (380 mg, 1.6 mmol) in DMF (10 mL) was treated slowly with a solution of 5-(chloromethyl)-1,2,3-trimethoxybenzene (344 mg, 1.6 mmol) in DMF (5 mL), heated to 120° C. for hour, cooled to room temperature, and partitioned between ethyl acetate and brine. The aqueous layer was extracted with ethyl acetate, and the combined extracts were washed with water and brine, dried (MgSO$_4$), filtered, and concentrated. The concentrate was purified by flash column chromatography on silica gel with 10% ethyl acetate/dichloromethane to provide the desired product.

EXAMPLE 96C 2-methoxy-5-((3,4,5-trimethoxybenzyl)sulfonyl) aniline

The desired product was prepared by substituting Example 96B for Example 90A in Example 90B.
MS (DCI/NH$_3$) m/e 385 (M+NH$_4$)$^+$;
$^1$H NMR (300 MHz, DMSO-d$_6$) δ6.98–6.85 (m, 3H), 6.37 (s, 2H), 5.21 (s, 2H), 4.38 (s, 2H), 3.84 (s, 3H), 3.63 (s, 9H);
Anal. calcd. for C$_{17}$H$_{21}$NO$_6$S: C, 55.57; H, 5.76; N, 3.81. Found: C, 55.52; H, 5.77; N, 3.49.

EXAMPLE 97

2-methoxy-5-((1-methyl-1-(3,4,5-trimethoxyphenyl) ethyl)sulfonyl)aniline

EXAMPLE 97A 1,2,3-trimethoxy-5-(1-((4-methoxy-3-nitrophenyl) sulfonyl)-1-methylethyl)benzene The desired product was prepared by substituting Example 96B for Example 87 in Example 88.

EXAMPLE 97B 2-methoxy-5-((1-methyl-1-(3,4,5-trimethoxyphenyl) ethyl)sulfonyl)aniline The desired product was prepared by substituting Example 97A for Example 90A in Example 90B.

MS (DCI/NH$_3$) m/e 413 (M+NH$_4$)$^+$;
$^1$H NMR (300 MHz, DMSO-d$_6$) δ6.87 (d, J=8 Hz, 1H), 6.78 (d, J=8 Hz, 1H), 6.59 (dd, J=3 Hz, 8Hz, 1H), 6.51 (s, 2H), 5.13 (s; 2H), 3.82 (s, 3H), 3.67 (s, 9H), 1.69 (s, 6H).

EXAMPLE 98

1,2,3-trimethoxy-5-((phenylsulfonyl)methyl)benzene

The desired product was prepared by substituting sodium benzenesulfinate for Example 96A in Example 96B.
MS (DCI/NH$_3$) m/e 340 (M+NH$_4$)$^+$;
$^1$H NMR (300 MHz, DMSO-d$_6$) δ7.72–7.57 (m, 5H), 6.38 (s, 2H), 4.58 (s, 2H), 3.64 (s, 3H), 3.40 (s, 6H).

Following Scheme 1 and the examples described above, the following compounds can be prepared:

EXAMPLE 99

N-(2-aminoacetyl)-1-methyl-N-(3,4,5-trimethoxyphenyl)-1H-indole-5-sulfonamide

EXAMPLE 100

N-(2-aminoacetyl)-3,4,5-trimethoxy-N-(1-methyl-1H-indol-5-yl)benzenesulfonamide

EXAMPLE 101

N-((2S)-2-aminopropanoyl]-1-methyl-N-(3,4,5-trimethoxyphenyl)-1H-indole-5-sulfonamide

EXAMPLE 102

N-((2S)-2-aminopropanoyl]-3,4,5-trimethoxy-N-(1-methyl-1H-indol-5-yl)benzenesulfonamide

EXAMPLE 103

N-(3-aminopropanoyl)-1-methyl-N-(3,4,5-trimethoxyphenyl)-1H-indole-5-sulfonamide

EXAMPLE 104

N-(3-aminopropanoyl)-3,4,5-trimethoxy-N-(1-methyl-1H-indol-5-yl)benzenesulfonamide

EXAMPLE 105

(2S)-2-amino-N-((1S)-1-methyl-2-oxo-2-(3,4,5-trimethoxy((1-methyl-1H-indol-5-yl)sulfonyl) anilino)ethyl)propanamide

EXAMPLE 106

(2S)-2-amino-N-((1S)-1-methyl-2-((1-methyl-1H-indol-5-yl)((3,4,5-trimethoxyphenyl)sulfonyl) amino)-2-oxoethyl)propanamide

EXAMPLE 107

N-((2S)-2-amino-3-hydroxypropanoyl)-1-methyl-N-(3,4,5-trimethoxyphenyl)-1H-indole-5-sulfonamide

EXAMPLE 108

N-((2S)-2-amino-3-hydroxypropanoyl)-3,4,5-trimethoxy-N-(1-methyl-1H-indol-5-yl) benzenesulfonamide

What is claimed is:
1. A compound having formula (I)

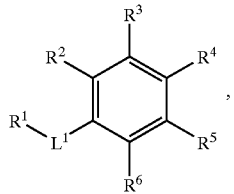

or a pharmaceutically acceptable salt or prodrug thereof, wherein $L^1$ is shown with its left end attached to $R^1$ and its right end attached to the phenyl ring and is —$SO_2NR^7$—, wherein $R^7$ is selected from the group consisting of
(a) hydrogen,
(b) hydroxy,
(c) amidinyl,
(d) a nitrogen-protecting group,
(e) alkanoyl,
(f) alkyl,
(g) alkenyl,
(h) alkynyl,
(i) cycloalkyl,
(j) cycloalkylalkyl,
(k) cycloalkenyl,
(l) cycloalkenylalkyl,
(m) aryloyl,
(n) alkoxy,
wherein (e)–(n) can be optionally substituted with one, two, or three substituents independently selected from the group consisting of
(i) hydroxyl,
(ii) halo,
(iii) cyano,
(iv) azido,
(v) carboxy,
(vi) amidinyl,
(vii) alkyl,
(viii) aryl,
(ix) oxo,
(x) heteroaryl,
(xi) heterocycloalkyl,
(xii) —$NR^cR^d$, wherein $R^c$ and $R^d$ are independently selected from the group consisting of
(1') hydrogen,
(2') alkyl,
(3') aryl, and
(4') alkoxyalkyl, and
(xiii) -(alkylene)—$NR^cR^d$,
wherein for (x) and (xi), the heteroaryl and the heterocycloalkyl can be optionally substituted with 1, 2, or 3 substituents independently selected from the group consisting of
(1') alkyl, and
(2') a nitrogen protecting group,
(o) heterocycloalkyloyl, wherein the heterocycloalkyloyl can be optionally substituted with 1, 2, or 3 substituents independently selected from the group consisting of
(i) alkyl, and
(ii) a nitrogen protecting group, and
(p) —$(CH_2)_xNR^AR^B$ wherein x is 0–6, and $R^A$ and $R^B$ are independently selected from the group consisting of
(i) hydrogen,
(ii) alkyl,
(iii) alkenyl,
(iv) alkynyl,
(v) cycloalkyl,
(vi) cycloalkylalkyl,
(vii) cycloalkenyl, and
(viii) cycloalkenylalkyl;

$R^1$ is indolyl, wherein the indolyl can be optionally substituted with 1, 2, 3, 4, or 5 substituents independently selected from the group consisting of
(a) oxo,
(b) azido,
(c) carboxy,
(d) carboxaldehyde,
(e) cyano,
(f) halo,
(g) hydroxy,
(h) nitro,
(i) perfluoroalkyl,
(j) perfluoroalkoxy,
(k) alkyl,
(l) alkenyl,
(m) alkynyl,
(n) alkanoyloxy,
(o) alkoxycarbonyl,
(p) cycloalkyl,
(q) cycloalkylalkyl,
(r) cycloalkenyl,
(s) cycloalkenylalkyl,
(t) alkanoyl,
(u) alkoxy,
(v) cycloalkoxy,
(w) aryloxy,
(x) heteroaryloxy,
(y) thioalkoxy,
(z) alkylsulfinyl,
(aa) alkylsulfonyl,
(bb) —$NR^8R^9$, wherein $R^8$ and $R^9$ are independently selected from the group consisting of
(i) hydrogen
(ii) alkyl,
(iii) arylalkyl, and
(iv) alkanoyl, wherein the alkanoyl can be optionally substituted with 1 or 2 substituents independently selected from the group consisting of
(1') halo
(2') hydroxy, and
(3') —$NR^{10}R^{11}$ wherein $R^{10}$ and $R^{11}$ are independently hydrogen or alkyl, and
(cc) —$SO_2NR^8R^9$, wherein $R^8$ and $R^9$ are defined above;

$R^2$ and $R^6$ are independently selected from the group consisting of
(1) hydrogen,
(2) alkyl,
(3) alkoxy,
(4) thioalkoxy; and
(5) hydroxy; and

53

$R^3$, $R^4$, and $R^5$ are independently selected from the group consisting of
(1) alkyl,
(2) alkoxy,
(3) thioalkoxy, and
(4) hydroxy.

2. A compound according to claim 1, wherein $R^2$ and $R^6$ are hydrogen, and $R^3$, $R^4$, and $R^5$ are methoxy.

3. A compound according to claim 1, wherein $R^1$ is optionally substituted indolyl.

4. A compound according to claim 3, wherein $R^1$ is optionally substituted 1H-indol-3-yl.

5. A compound according to claim 4 selected from the group consisting of 5-nitro-N-(3,4,5-trimethoxyphenyl)-1H-indole-3-sulfonamide,
1-methyl-5-nitro-N-(3,4,5-trimethoxyphenyl)-1H-indole-3-sulfonamide,
5-amino-1-methyl-N-(3,4,5-trimethoxyphenyl)-1H-indole-3-sulfonamide, and
5-amino-N-(3,4,5-trimethoxyphenyl)-1H-indole-3-sulfonamide.

6. A compound according to claim 3, wherein $R^1$ is optionally substituted 1H-indol-5-yl.

7. A compound according to claim 6 selected from the group consisting of

N-(3,4,5-trimethoxyphenyl)-1H-indole-5-sulfonamnide,
1-methyl-N-(3,4,5-trimethoxyphenyl)-1H-indole-5-sulfonamide,
N,1-dimethyl-N-(3,4,5-trimethoxyphenyl)-1H-indole-5-sulfonamide,
1-ethyl-N-(3,4,5-trimethoxyphenyl)-1H-indole-5-sulfonamide,
N-(2-hydroxyethyl)-1-methyl-N-(3,4,5-trimethoxyphenyl)-1H-indole-5-sulfonamide,
N-(2-fluoroethyl)-1-methyl-N-(3,4,5-trimethoxyphenyl)-1H-indole-5-sulfonamide,
N-ethyl-1-methyl-N-(3,4,5-trimethoxyphenyl)-1H-indole-5-sulfonamide,
N-((dimethylamino)acetyl)-1-methyl-N-(3,4,5-trimethoxyphenyl)-1H-indole-5-sulfonamide,
1-methyl-N-(((2S)-1-methylpyrrolidinyl)carbonyl)-N-(3,4,5-trimethoxyphenyl)-1H-indole-5-sulfonamide,
N-((2S)-2-(dimethylamino)-3-methylbutanoyl)-1-methyl-N-(3,4,5-trimethoxyphenyl)-1H-indole-5-sulfonamide,
N-((2S)-2-amino-3-methylbutanoyl)-1-methyl-N-(3,4,5-trimethoxyphenyl)-1H-indole-5-sulfonamide,
1-methyl-N-((2S)-2-methylamino)propanoyl)-N-(3,4,5-trimethoxyphenyl)-1H-indole-5-sulfonamide,
N-((2S)-2-amino-2-phenylethanoyl)-1-methyl-N-(3,4,5-trimethoxyphenyl)-1H-indole-5-sulfonamide,
N-((2S)-2-amino-3-phenylpropanoyl)-1-methyl-N-(3,4,5-trimethoxyphenyl)-1H-indole-5-sulfonamide,
1-methyl-N-((2S)-pyrrolidinylcarbonyl)-N-(3,4,5-trimethoxyphenyl)-1H-indole-5-sulfonamide,
N-((2S)-2,6-diaminohexanoyl)-1-methyl-N-(3,4,5-trimethoxyphenyl)-1H-indole-5-sulfonamide,
N-((2S)-2-amino-3-(1H-imidazol-5-yl)propanoyl)-1-methyl-N-(3,4,5-trimethoxyphenyl)-1H-indole-5-sulfonamide,
(2S)-2-amino-4-oxo-4-(3,4,5-trimethoxy((1-methyl-1H-indol-5-yl)sulfonyl)anilino)butanoic acid,
(3S)-3-amino4-oxo-4-(3,4,5-trimethoxy((1-methyl-1H-indol-5-yl)sulfonyl)anilino)butanoic acid,
(2S)-2-amino-5-oxo-5-(3,4,5-trimethoxy((1-methyl-1H-indol-5-yl)sulfonyl)anilino)pentanoic acid,

54

(4S)-4-amino-5-oxo-5-(3,4,5-trimethoxy((1-methyl-1H-indol-5-yl)sulfonyl)anilino)pentanoic acid,
N-((bis(2-methoxyethyl)amino)acetyl)-1-methyl-N-(3,4,5-trimethoxyphenyl)-1H-indole-5-sulfonamide,
1-methyl-N-(4-morpholinylacetyl)-N-(3,4,5-trimethoxyphenyl)-1H-indole-5-sulfonamide,
1-methyl-N-((4-methyl-1-piperazinyl)acetyl)-N-(3,4,5-trimethoxyphenyl)-1H-indole-5-sulfonamide,
N-(4-(aminomethyl)benzoyl)-1-methyl-N-(3,4,5-trimethoxyphenyl)-1H-indole-5-sulfonamide,
N-(2-aminoacetyl)-1-methyl-N-(3,4,5-trimethoxyphenyl)-1H-indole-5-sulfonamide,
N-((2S)-2-aminopropanoyl]-1-methyl-N-(3,4,5-trimethoxyphenyl)-1H-indole-5-sulfonamide,
N-(3-aminopropanoyl)-1-methyl-N-(3,4,5-trimethoxyphenyl)-1H-indole-5-sulfonamide,
(2S)-2-amino-N-((1S)-1-methyl-2-oxo-2-(3,4,5-trimethoxy((1-methyl-1H-indol-5-yl)sulfonyl)anilino)ethyl)propanamide, and
N-((2S)-2-amino-3-hydroxypropanoyl)-1-methyl-N-(3,4,5-trimethoxyphenyl)-1H-indole-5-sulfonamide.

8. A method of inhibiting polymerization of tubulin in a mammal comprising administering an effective amount of a compound of claim 1.

9. A method of treating cancer in a mammal in need of such treatment comprising administering an effective amount of a compound of claim 1.

10. A compound selected from the group consisting of 5-nitro-N-(3,4,5-trimethoxyphenyl)-1H-indole-3-sulfonamide,
1-methyl-5-nitro-N-(3,4,5-trimethoxyphenyl)-1H-indole-3-sulfonamide,
5-amino-1-methyl-N-(3,4,5-trimethoxyphenyl)-1H-indole-3-sulfonamide,
5-amino-N-(3,4,5-trimethoxyphenyl)-1H-indole-3-sulfonamide,
N-(3,4,5-trimethoxyphenyl)-1H-indole-5-sulfonamide,
1-methyl-N-(3,4,5-trimethoxyphenyl)-1H-indole-5-sulfonamide,
N,1-dimethyl-N-(3,4,5-trimethoxyphenyl)-1H-indole-5-sulfonamide,
1-ethyl-N-(3,4,5-trimethoxyphenyl)-1H-indole-5-sulfonamide,
N-(2-hydroxyethyl)-1-methyl-N-(3,4,5-trimethoxyphenyl)-1H-indole-5-sulfonamide,
N-(2-fluoroethyl)-1-methyl-N-(3,4,5-trimethoxyphenyl)-1H-indole-5-sulfonamide,
N-ethyl-1-methyl-N-(3,4,5-trimethoxyphenyl)-1H-indole-5-sulfonamide,
N-((dimethylamino)acetyl)-1-methyl-N-(3,4,5-trimethoxyphenyl)-1H-indole-5-sulfonamide,
1-methyl-N-(((2S)-1-methylpyrrolidinyl)carbonyl)-N-(3,4,5-trimethoxyphenyl)-1H-indole-5-sulfonamide,
N-((2S)-2-(dimethylamino)-3-methylbutanoyl)-1-methyl-N-(3,4,5-trimethoxyphenyl)-1H-indole-5-sulfonamide,
N-((2S)-2-amino-3-methylbutanoyl)-1-methyl-N-(3,4,5-trimethoxyphenyl)-1H-indole-5-sulfonamide,
1-methyl-N-((2S)-2-methylamino)propanoyl)-N-(3,4,5-trimethoxyphenyl)-1H-indole-5-sulfonamide,
N-((2S)-2-amino-2-phenylethanoyl)-1-methyl-N-(3,4,5-trimethoxyphenyl)-1H-indole-5-sulfonamide,
N-((2S)-2-amino-3-phenylpropanoyl)-1-methyl-N-(3,4,5-trimethoxyphenyl)-1H-indole-5-sulfonamide,
1-methyl-N-((2S)-pyrrolidinylcarbonyl)-N-(3,4,5-trimethoxyphenyl)-1H-indole-5-sulfonamide,
N-((2S)-2,6-diaminohexanoyl)-1-methyl-N-(3,4,5-trimethoxyphenyl)-1H-indole-5-sufonamide,.

N-((2S)-2-amino-3-(1H-imidazol-5-yl)propanoyl)-1-methyl-N-(3,4,5-trimethoxyphenyl)-1H-indole-5-sulfonamide, (2S)-2-amino-4-oxo-4-(3,4,5-trimethoxy((1-methyl-1H-indol-5-yl)sulfonyl)anilino)butanoic acid, (3S)-3-amino-4-oxo-4-(3,4,5-trimethoxy((1-methyl-1H-indol-5-yl)sulfonyl)anilino)butanoic acid, (2S)-2-amino-5-oxo-5-(3,4,5-trimethoxy((1-methyl-1H-indol-5-yl)sulfonyl)anilino)pentanoic acid, (4S)-4-amino-5-oxo-5-(3,4,5-trimethoxy((1-methyl-1H-indol-5-yl)sulfonyl)anilino)pentanoic acid, N-((bis(2-methoxyethyl)amino)acetyl)-1-methyl-N-(3,4,5-trimethoxyphenyl)-1H-indole-5-sulfonamide, 1-methyl-N-(4-morpholiniylacetyl)-N-(3,4,5-trimethoxyphenyl)-1H-indole-5-sulfonamide, 1-methyl-N-((4-methyl-1-piperazinyl)acetyl)-N-(3,4,5-trimethoxyphenyl)-1H-indole-5-sulfonamide, and N-(4-(aminomethyl)benzoyl)-1-methyl-N-(3,4,5-trimethoxyphenyl)-1H-indole-5-sulfonamide.

11. A compound which is

N-((dimethylamino)acetyl)-1-methyl-N-(3,4,5-trimethoxyphenyl)-1H-indole-5-sulfonamide.

* * * * *

UNITED STATES PATENT AND TRADEMARK OFFICE
CERTIFICATE OF CORRECTION

PATENT NO. : 6,521,658 B1
DATED : February 18, 2003
INVENTOR(S) : Qun Li et al.

It is certified that error appears in the above-identified patent and that said Letters Patent is hereby corrected as shown below:

Column 53,
Line 9, replace "The word "claim 1"" with -- The word "claim 2" --.

Signed and Sealed this

Twenty-seventh Day of May, 2003

JAMES E. ROGAN
*Director of the United States Patent and Trademark Office*